United States Patent
Lagrange et al.

(10) Patent No.: US 12,064,500 B2
(45) Date of Patent: *Aug. 20, 2024

(54) HAIR LIGHTENING COMPOSITION COMPRISING HYDROGEN PEROXIDE, A PEROXYGENATED SALT, A CARBONATE AND AT LEAST ONE POLYPHOSPHORUS DERIVATIVE

(71) Applicant: L'OREAL, Paris (FR)

(72) Inventors: Alain Lagrange, Saint-Ouen (FR); Boris Lalleman, Saint-Ouen (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/468,354

(22) PCT Filed: Dec. 19, 2017

(86) PCT No.: PCT/EP2017/083426
§ 371 (c)(1),
(2) Date: Jun. 11, 2019

(87) PCT Pub. No.: WO2018/114876
PCT Pub. Date: Jun. 28, 2018

(65) Prior Publication Data
US 2020/0129392 A1    Apr. 30, 2020

(30) Foreign Application Priority Data

Dec. 20, 2016 (FR) ...................................... 1662863

(51) Int. Cl.
| | | |
|---|---|---|
| *A61K 8/22* | (2006.01) | |
| *A61K 8/19* | (2006.01) | |
| *A61K 8/23* | (2006.01) | |
| *A61K 8/24* | (2006.01) | |
| *A61K 8/31* | (2006.01) | |
| *A61K 8/34* | (2006.01) | |
| *A61K 8/46* | (2006.01) | |
| *A61K 8/55* | (2006.01) | |
| *A61Q 5/08* | (2006.01) | |

(52) U.S. Cl.
CPC ................. *A61K 8/22* (2013.01); *A61K 8/19* (2013.01); *A61K 8/23* (2013.01); *A61K 8/24* (2013.01); *A61K 8/31* (2013.01); *A61K 8/34* (2013.01); *A61K 8/347* (2013.01); *A61K 8/463* (2013.01); *A61K 8/55* (2013.01); *A61Q 5/08* (2013.01); *A61K 2800/882* (2013.01)

(58) Field of Classification Search
CPC ... A61K 8/22; A61K 8/19; A61K 8/23; A61K 8/24; A61K 8/31; A61K 8/34; A61K 8/347; A61K 8/463; A61K 8/55; A61K 2800/882; A61Q 5/08
See application file for complete search history.

(56) References Cited

U.S. PATENT DOCUMENTS

| | | | |
|---|---|---|---|
| 3,376,110 A | 4/1968 | Shiraeff | |
| 3,997,659 A | 12/1976 | Knohl et al. | |
| 4,137,180 A | 1/1979 | Naik et al. | |
| 4,138,478 A | 2/1979 | Reese et al. | |
| 4,874,554 A | 10/1989 | Lange et al. | |
| 5,008,093 A | 4/1991 | Merianos | |
| 5,183,901 A | 2/1993 | Login et al. | |
| 5,708,151 A | 1/1998 | Möckli | |
| 7,740,663 B2 * | 6/2010 | De La Mettrie | A61Q 5/08 8/107 |
| 7,766,976 B2 * | 8/2010 | Bureiko | A61K 8/8152 8/405 |
| 7,799,095 B2 * | 9/2010 | Mario | A61Q 5/10 8/405 |
| 2004/0076594 A1 * | 4/2004 | Legrand | A61K 8/25 424/62 |
| 2004/0098816 A1 | 5/2004 | Au et al. | |

(Continued)

FOREIGN PATENT DOCUMENTS

| | | |
|---|---|---|
| CN | 103491822 A | 1/2014 |
| CN | 104446345 A | 3/2015 |

(Continued)

OTHER PUBLICATIONS

International Search Report and Written Opinion for counterpart Application No. PCT/EP2017/083421, mailed Feb. 9, 2018.
International Search Report and Written Opinion for counterpart Application No. PCT/EP2017/083420, mailed Mar. 2, 2018.
International Search Report and Written Opinion for counterpart Application No. PCT/EP2017/083424, mailed Feb. 1, 2018.
International Search Report and Written Opinion for counterpart Application No. PCT/EP2017/083426, mailed Feb. 15, 2018.

(Continued)

*Primary Examiner* — Robert A Wax
*Assistant Examiner* — Olga V. Tcherkasskaya
(74) *Attorney, Agent, or Firm* — The Marbury Law Group PLLC

(57) ABSTRACT

The present disclosure relates to a composition for lightening keratin fibres, comprising (a) hydrogen peroxide; (b) one or more carbonates and/or one or more carbonate-generating systems in a content of greater than or equal to 0.2%, relative to the weight of the composition, (c) one or more polyphosphorus derivatives, in a total content of greater than or equal to 0.5% by weight, relative to the total weight of the composition, and (d) one or more peroxygenated salts, said polyphosphorus derivative(s) being different from said peroxygenated salt(s). The pH of the composition is less than or equal to 10. The present disclosure also relates to a process of using the composition for lightening keratin fibres, and a device comprising the composition.

22 Claims, No Drawings

(56) References Cited

U.S. PATENT DOCUMENTS

| | | | |
|---|---|---|---|
| 2005/0191251 A1* | 9/2005 | Kravtchenko | A61Q 5/08 424/62 |
| 2006/0117493 A1* | 6/2006 | Bureiko | A61K 8/731 8/405 |
| 2006/0234893 A1 | 10/2006 | Busch et al. | |
| 2007/0107143 A1 | 5/2007 | Boswell et al. | |
| 2010/0226864 A1 | 9/2010 | Oertling et al. | |
| 2013/0042883 A1* | 2/2013 | DeGeorge | A61K 8/23 132/208 |
| 2014/0130823 A1 | 5/2014 | Iizaki et al. | |
| 2014/0311517 A1* | 10/2014 | Degeorge | A61Q 5/10 132/208 |
| 2015/0056151 A1 | 2/2015 | Deconinck | |
| 2015/0272849 A1 | 10/2015 | Neuba et al. | |

FOREIGN PATENT DOCUMENTS

| | | |
|---|---|---|
| DE | 2549294 A1 | 5/1977 |
| DE | 29613065 | 11/1997 |
| DE | 10 2008 017439 A1 | 10/2009 |
| DE | 10 2012 223207 A1 | 6/2014 |
| EP | 0714954 A2 | 6/1996 |
| EP | 1669106 A1 | 6/2006 |
| EP | 2005854 A1 | 12/2008 |
| FR | 1070766 A | 8/1954 |
| FR | 2132213 A1 | 11/1972 |
| FR | 2814943 A1 | 4/2002 |
| FR | 2961397 A1 | 12/2011 |
| FR | 2971158 A1 | 8/2012 |
| GB | 2217735 A | 11/1989 |
| JP | 2004-161707 A | 6/2004 |
| JP | 2004-262854 A | 9/2004 |
| JP | 2004-359483 A | 12/2004 |
| JP | 2005-206514 A | 8/2005 |
| JP | 2012-236016 A | 12/2012 |
| WO | 95/01772 A1 | 1/1995 |
| WO | 95/15144 A1 | 6/1995 |
| WO | 2011/157699 A2 | 12/2011 |
| WO | 2014/207097 A1 | 12/2014 |
| WO | 2018/046170 A1 | 3/2018 |
| WO | 2018/114872 A1 | 6/2018 |
| WO | 2018/114873 A1 | 6/2018 |
| WO | 2018/114875 A1 | 6/2018 |

OTHER PUBLICATIONS

Hansen, C.M., "Hansen Solubility Parameters A User's Handbook," CRC Press LLC, 2000, pp. 167-185.
Porter, M.R., "Handbook of Surfactants," published by Blackie & Son (Glasgow and London), 1991, pp. 116-178.
Todd, Charles, et al., "Volatile Silicone Fluids for Cosmetic Formulations," Cosmetics and Toiletries, vol. 91, Jan. 1976, pp. 29-32.
Barton, "Handbook of Solubility Parameters and Other Cohesion Parameters," CRC Press, Second Edition, 1991, pp. 95-121 and 177-193.
Mintel: "Hair Lightening Kit," Wella, XP002769345, Apr. 1, 2005.
Translated Japanese Office Action for counterpart Application No. 2019-532762, dated Jul. 20, 2020.
Translated Japanese Office Action for counterpart Application No. 2019-532756, dated Jul. 20, 2020.
Translated Japanese Office Action for counterpart Application No. 2019-532794, dated Jul. 20, 2020.
Translated Japanese Office Action for counterpart Application No. 2019-532800, dated Jul. 20, 2020.
Non-Final Office Action for copending U.S. Appl. No. 16/468,353, dated Jun. 24, 2021.
Non-Final Office Action for copending U.S. Appl. No. 16/468,351, dated May 5, 2021.
Final Office Action for copending U.S. Appl. No. 16/468,351, dated Oct. 27, 2021.
Final Office Action for copending U.S. Appl. No. 16/468,353, dated Dec. 13, 2021.
Translated Chinese Office Action for counterpart Application No. 201780078394.4, dated Aug. 31, 2021.
Translated Chinese Office Action for Application No. 201780078395.9, dated Jul. 28, 2021.
Translated Chinese Office Action for counterpart Application No. 201780078041.4, dated Jul. 27, 2021.
Jai-han et al., "Use of Sodium Pyrophosphate in Oxygen Bleaching," Beijing Textile, Dec. 31, 1991, pp. 38-39 (no translation).
Non-Final Office Action for copending U.S. Appl. No. 16/468,351, dated Jun. 22, 2022.
Non-Final Office Action for copending U.S. Appl. No. 16/468,353, dated Jul. 20, 2022.
Non-Final Office Action for copending U.S. Appl. No. 16/468,349, dated Aug. 3, 2022.
Translation of Notice of Reasons for Refusal for counterpart Japanese Application No. 2021-176657, dated Oct. 17, 2022.
Non-Final Office Action for copending U.S. Appl. No. 16/468,351, dated May 24, 2023.
Final Office Action for copending U.S. Appl. No. 16/468,349, dated Feb. 21, 2023.
Office Action in 16468353, mailed Mar. 22, 2024, 13 pages.
Final Office Action for copending U.S. Appl. No. 16/468,353, dated Sep. 7, 2023.
Karlheinz Schrader: Grundlagen und Rezepturen der Kosmetika, 2. Auflage, Heidelberg, 1989, Seiten 815-823, 294-295 (translation unavailable).
Translation of communication from Henkel AG to European Patent Office in Opposition of counterpart Application No. EP 3558218B1, dated Feb. 2, 2023.
Final Office Action in U.S. Appl. No. 16/468,351, mailed Dec. 28, 2023, 20 pages.

* cited by examiner

HAIR LIGHTENING COMPOSITION COMPRISING HYDROGEN PEROXIDE, A PEROXYGENATED SALT, A CARBONATE AND AT LEAST ONE POLYPHOSPHORUS DERIVATIVE

The present invention relates to a composition for lightening keratin materials, preferably keratin fibres, in particular human keratin fibres such as the hair, comprising (a) hydrogen peroxide; (b) one or more carbonates and/or one or more carbonate-generating systems in a content of greater than or equal to 0.2% by weight relative to the weight of the composition, (c) one or more polyphosphorus derivatives, in a total content of greater than or equal to 0.5% by weight, relative to the total weight of the composition, (d) one or more peroxygenated salts, said polyphosphorus derivative(s) being different from said peroxygenated salt(s), and the pH of the composition being less than or equal to 10, preferably less than or equal to 9.7, preferably less than or equal to 9.5.

The invention also relates to a lightening process using said composition, and also to a multi-compartment device which is suitable for using said lightening composition.

The present invention relates to the field of the lightening of keratin materials, preferably of keratin fibres and more particularly to the field of lightening the hair.

The lightening of hair is evaluated by the "tone depth", which characterizes the degree or level of lightening. The notion of "tone" is based on the classification of natural shades, one tone separating each shade from the shade immediately following or preceding it. This definition and the classification of natural shades are well known to hair-styling professionals and are published in the publication *Sciences des traitements capillaires* [Hair treatment science] by Charles Zviak, 1988, published by Masson, pages 215 and 278.

Tone depths range from 1 (black) to 10 (very light blond), one unit corresponding to one tone; the higher the figure, the lighter the shade.

Lightening makes it possible to afford a lighter tone depth than the initial natural tone depth of the head of hair, which is particularly sought by consumers.

The processes for lightening human keratin fibres that are usually employed consist in using an aqueous composition comprising at least one oxidizing agent, under alkaline pH conditions in the vast majority of cases. This oxidizing agent has the role of degrading the melanin of the hair, which, depending on the nature of the oxidizing agent present, leads to more or less pronounced lightening of the fibres. Thus, for relatively mild lightening, the oxidizing agent is generally hydrogen peroxide. When more pronounced lightening is desired, use is usually made of peroxygenated salts, for instance persulfates, in the presence of hydrogen peroxide.

One of the difficulties arises from the fact that the lightening process is generally performed under highly alkaline conditions and that the alkaline agent most commonly used is aqueous ammonia. The use of aqueous ammonia is particularly advantageous in processes of this type. Specifically, it makes it possible to adjust the pH of the composition to an alkaline pH to enable activation of the oxidizing agent. However, this alkaline agent also causes swelling of the keratin fibre, with opening of the scales, which promotes the penetration of the oxidizing agent into the fibre, and thus increases the efficacy of the reaction.

However, this basifying agent is highly volatile, and this causes unpleasantness to the user on account of the strong and fairly unpleasant characteristic odour of ammonia that is given off during the process.

Furthermore, the amount of ammonia given off requires the use of higher contents than necessary in order to compensate for this loss. This is not without consequences for the user, who not only remains inconvenienced by the odour, but may also be confronted with greater risks of intolerance, for instance irritation of the scalp, which is reflected especially by stinging.

Furthermore, the use of aqueous ammonia and of persulfates is not without consequences for the integrity of the hair fibre and may lead to impairment of the quality of the hair. The essential causes of this impairment of the quality of the hair are a decrease in its cosmetic properties, such as its sheen, and degradation of its mechanical properties, more particularly degradation of its mechanical strength, which may also be reflected by an increase in its porosity. The hair is weakened and may become brittle during subsequent treatments such as blow-drying.

It has also been proposed to replace all or some of the aqueous ammonia with one or more other standard basifying agents, such as alkanolamines, but the solutions proposed hitherto do not result in compositions that are as effective as those based on aqueous ammonia, especially since these basifying agents do not provide sufficient lightening of pigmented fibres in the presence of the oxidizing agent. Furthermore, monoethanolamine, when used at high concentrations, may cause irritation of the scalp.

Thus, the hair-lightening technique, which must make it possible to obtain sufficient lightening of the fibre, generally involves using either aqueous ammonia or monoethanolamine, or else a mixture of monoethanolamine and aqueous ammonia, as basifying agent as a mixture with aqueous hydrogen peroxide solution.

Thus, one of the objectives of the present invention is to propose compositions for lightening keratin materials, preferably human keratin fibres such as the hair, which do not have the drawbacks mentioned above, i.e. which are capable of producing very good lightening performance while at the same time having working qualities that are superior to those of the existing compositions, especially while having a less disagreeable odour during their application to the fibres or during their preparation, and which are well tolerated by the scalp and respect the nature of the hair (integrity and sensory nature of the fibre).

In particular, the process according to the invention makes it possible to obtain good levels of lightening (power of the lightening obtained) with compositions comprising low contents of peroxygenated salts and/or whose pH may be less alkaline (i.e. closer to 7) than the compositions of the prior art.

These aims and others are achieved by the present invention, one subject of which is thus a cosmetic composition for lightening keratin materials, preferably keratin fibres, in particular human keratin fibres such as the hair, comprising:
  (a) hydrogen peroxide,
  (b) one or more carbonates and/or one or more carbonate-generating systems in a content of greater than or equal to 0.2%, preferably greater than or equal to 0.3%, preferably greater than or equal to 0.5% and particularly greater than or equal to 1% by weight relative to the weight of the composition,
  (c) one or more polyphosphorus derivatives preferably chosen from linear or cyclic compounds comprising at least two phosphorus atoms covalently bonded together via at least one linker L comprising at least one oxygen atom and/or at least one carbon atom, preferably at least one oxygen atom, said polyphosphorus derivative(s) being present in a total content of greater than or equal to 0.5% by weight, relative to the total weight of the composition,
(d) one or more peroxygenated salts;
said polyphosphorus derivative(s) being different from said peroxygenated salt(s), and the pH of the composition being less than or equal to 10, preferably less than or equal 35 to 9.7, and better still less than or equal to 9.5.

Preferably, the pH of the composition ranges from 6 to 9.7 and better still from 6 to 9.5.

For the purposes of the present invention, the term "composition for lightening" or "lightening composition" means a ready-to-use composition which is applied to keratin materials, preferably to keratin fibres. The lightening composition may be prepared just before application to said fibres.

A subject of the present invention is also a process for lightening keratin materials, preferably keratin fibres, in particular human keratin fibres such as the hair.

The invention also relates to a multi-compartment device for using the composition according to the invention.

The compositions according to the invention thus make it possible to produce very good lightening performance on keratin fibres, especially in terms of the level of lightening and the homogeneity of lightening, and also in terms of neutralization of glints (especially as regards the colour parameter b* in the Commission Internationale de l'Elcairage (CIE) L*a*b* colour evaluation system) while at the same time preserving the integrity of the fibre (limiting the amount of breakage of the fibres) and conserving good sensory qualities of the fibre.

Moreover, the lightening process according to the invention also allows the use of compositions that do not have the drawbacks associated with odour during their application to keratin fibres or during their preparation.

Other characteristics and advantages of the invention will emerge more clearly on reading the description and the examples that follow.

In the text hereinbelow, and unless otherwise indicated, the limits of a range of values are included within that range.

The human keratin fibres treated via the process according to the invention are preferably the hair.

The expression "at least one" is equivalent to the expression "one or more".
(a) Chemical Oxidizing Agent The lightening composition according to the invention contains hydrogen peroxide as chemical oxidizing agent.

The term "chemical oxidizing agent" means an oxidizing agent other than atmospheric oxygen.
(b) Carbonate(s) and/or Carbonate-Generating System The lightening system according to the present invention comprises one or more carbonates and/or one or more carbonate-generating systems.

The carbonate(s) or the carbonate-generating system(s) may be used in one or more cosmetic compositions during the lightening process.

The term "carbonate-generating system" means a system which generates carbonate in situ, for instance carbon dioxide in water.

The carbonate(s) are preferably chosen from:
a) carbonates of alkali metals ($Met_2CO_3$), of alkaline-earth metals ($Met'CO_3$) or of phosphonium (($PR''_4)_2CO_3$) with Met' representing an alkaline-earth metal and Met representing an alkali metal, and R", which may be identical or different, representing a hydrogen atom or an optionally substituted ($C_1$-$C_6$) alkyl group such as hydroxyethyl; and mixtures thereof.

More particularly, the carbonate(s) are chosen from alkali metal and alkaline-earth metal carbonates; preferentially alkali metal carbonates, or mixtures thereof.

Preferably, they are chosen from carbonates of Na, K, Mg, Ca and mixtures thereof.

Preferably, the carbonate(s) are chosen from sodium carbonate and potassium carbonate, and mixtures thereof.

According to the invention, the carbonate agent(s) used represent a content of greater than or equal to 0.2%, preferably greater than or equal to 0.3%, preferably greater than or equal to 0.5% and particularly greater than or equal to 10% by weight relative to the weight of the composition.

According to the invention, the carbonate agent(s) used preferably represent a total content ranging from 0.2% to 20% by weight relative to the total weight of the composition according to the invention, preferably from 0.3% to 15% by weight, even more preferentially from 0.5% to 10% by weight, preferably from 1% to 10% by weight.

Preferably, the carbonate agent(s) used represent a total content of from 0.5% to 10% by weight and preferably from 1% to 10% by weight relative to the total weight of the composition according to the invention.
(c) Polyphosphorus Derivative(s)

In particular, the lightening composition according to the invention comprises c) one or more polyphosphorus derivatives in a total content of greater than or equal to 0.5% by weight relative to the total weight of the composition.

The term "polyphosphorus derivative" means a compound comprising at least two phosphorus atoms. More particularly, the term "polyphosphorus derivative" preferably means linear or cyclic compounds comprising at least two phosphorus atoms bonded together covalently via at least one linker L comprising at least one oxygen atom and/or at least one carbon atom. According to one embodiment, when the linker comprises at least one carbon atom, it may comprise at least one nitrogen atom.

Particularly preferably, the linker L of the polyphosphorus derivatives used according to the various subjects of the invention comprises at least one oxygen atom.

Preferably, the polyphosphorus derivative(s) used according to the present invention comprise less than 20 phosphorus atoms, preferably less than 15 phosphorus atoms, preferably less than 10 phosphorus atoms.

Preferably, the polyphosphorus derivative comprises at least two groups chosen from a group —P(R)(=O)—OH, a group —P(R)(=O)—O M, a group >P(=O)—OH and/or a group >P(=O)—O M, with:
  M representing a cationic counterion, preferably chosen from alkali metals and alkaline-earth metals,
  R representing a hydroxyl group, —OM, a ($C_1$-$C_6$)alkyl, ($C_1$-$C_6$)alkoxy, cycloalkyloxy or (hetero)aryloxy group, and
  > representing the two bonds connected to the phosphorus atom and forming part of a ring.

According to the present invention, said polyphosphorus derivative(s) are present in a total content of greater than or equal to 0.5% by weight relative to the total weight of the composition.

According to a preferred embodiment, the polyphosphorus derivative(s) are chosen from inorganic polyphosphorus derivatives.

According to another embodiment, the polyphosphorus derivative(s) are chosen from organic polyphosphorus derivatives.

Preferably, the polyphosphorus derivative(s) present in the compositions according to the invention are non-amine derivatives.

Preferably, the polyphosphorus derivative(s) c) as defined previously are chosen from polyphosphates and polyphosphonates, and mixtures thereof.

Preferably, the polyphosphorus derivative(s) are polyphosphates.

Preferably, the polyphosphorus derivative(s) c) as defined previously are chosen from:
inorganic polyphosphorus derivatives chosen from:
pyrophosphates, preferably in the form of salts, preferably of alkali metal salts, which may or may not be hydrated, such as sodium pyrophosphate, potassium pyrophosphate or sodium pyrophosphate decahydrate;
hexametaphosphates, preferably in the form of salts, preferably of alkali metal salts, which may or may not be hydrated, such as sodium hexametaphosphate;
tripolyphosphates, preferably in the form of salts, preferably of alkali metal salts, which may or may not be hydrated, such as sodium tripolyphosphate;
trimetaphosphates, preferably in the form of salts, preferably of alkali metal salts, which may or may not be hydrated, such as sodium trimetaphosphate; and mixtures thereof;
and organic polyphosphorus derivatives, preferably chosen from:
organic polyphosphate derivatives, such as polyphosphoric acids and/or salts thereof such as phytic acid (also known as myo-inositol hexaphosphoric acid);
organic polyphosphonate derivatives, such as polyphosphonic acids and/or salts thereof such as ethylenediamine tetra(methylene phosphonic acid) (EDTMP), diethylenetriaminepenta(methylene phosphonic acid) (DETMP), amino tri(methylene phosphonic acid) (ATMP), 1-Hydroxyethane-1,1-diphosphonic acid (HEDP), diethylenetriamine penta(methylene phosphonic acid) (DTPMP), and mixtures thereof,
and mixtures thereof.

Preferably, the polyphosphorus derivative(s) are chosen from:
inorganic polyphosphate derivatives chosen from hydrated or non-hydrated alkali metal pyrophosphates, such as sodium pyrophosphate, potassium pyrophosphate, sodium pyrophosphate decahydrate; and polyphosphates, such as sodium hexametaphosphate, sodium polyphosphate, sodium tripolyphosphate, sodium trimetaphosphate; and mixtures thereof,
and organic polyphosphorus derivatives chosen from organic polyphosphate derivatives such as polyphosphoric acids and/or salts thereof such as phytic acid (also known as myo-inositol hexaphosphoric acid), organic polyphosphonate derivatives such as polyphosphonic acids and/or salts thereof such as EDTMP, DETMP, ATMP, HEDP, DTPMP, and mixtures thereof,
and mixtures thereof.

Preferably, the polyphosphorus derivative(s) are chosen from inorganic polyphosphate derivatives, preferably from hydrated or non-hydrated alkali metal pyrophosphates, preferably from sodium pyrophosphate, potassium pyrophosphate and sodium pyrophosphate decahydrate.

Preferably, said polyphosphorus derivative(s) are chosen from compounds belonging to any one of formulae (I), (II) and (III) below; or mixtures thereof:

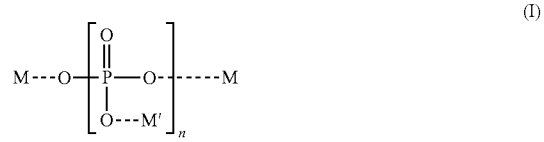

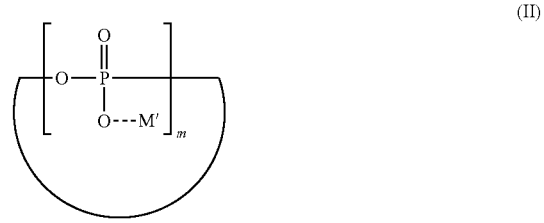

and also the solvates thereof such as hydrates;
with
n ranging from 2 to 10, preferably from 2 to 6 and better still from 2 to 3;
m ranging from 2 to 10, preferably from 2 to 6;
Y representing an alkyl chain comprising at least one phosphorus atom and optionally one or more non-phosphorus heteroatoms, or a cyclic carbon-based radical optionally comprising one or more heteroatoms, said hydrocarbon-based radical being substituted with one or more groups comprising one or more phosphorus atoms;
M or M' representing a hydrogen atom, an alkali metal or an alkaline-earth metal;
- - - - representing a single bond when M or M' is H, or an ionic bond.

It is understood that when M or M' is other than H, then M or M' are such that the overall charge of the molecule is zero. Thus, in the case of divalent metals, M and M' may represent the same divalent metal.

The polyphosphorus derivatives of formula (I) are linear.
The polyphosphorus derivatives of formula (II) are cyclic.
Preferably, according to a first embodiment, the polyphosphorus derivative(s) are inorganic polyphosphate compounds, preferably chosen from:
polyphosphates, and/or hydrates thereof; and mixtures thereof, preferably of sodium and/or potassium, such as sodium hexametaphosphate (SHMP),

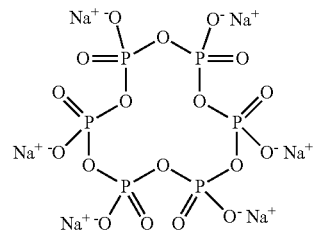

sodium polyphosphate, sodium tripolyphosphate, sodium trimetaphosphate, preferably sodium tripolyphosphate having the following formula:

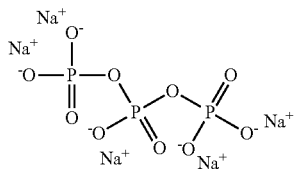

pyrophosphates and/or hydrates thereof, and mixtures thereof, preferably of sodium and/or potassium; preferably chosen from sodium pyrophosphate and/or potassium pyrophosphate, and hydrates thereof, such as sodium pyrophosphate decahydrate having the following formula:

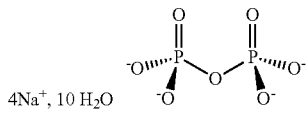

or potassium pyrophosphate having the following formula:

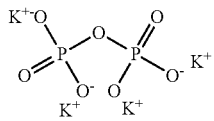

and mixtures thereof.

According to a second embodiment, the polyphosphorus derivative(s) are organic polyphosphate derivatives and/or organic polyphosphonate derivatives, preferably chosen from polyphosphoric acids and/or salts thereof, polyphosphonic acids and/or salts thereof such as EDTMP, DETMP, ATMP, HEDP, DTPMP

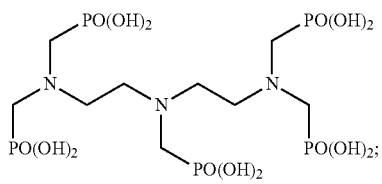

DETMP and mixtures thereof iminodi(methylphosphonic) acid (example L) or salts thereof, and mixtures thereof;

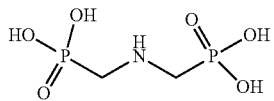

tetrasodium etidronate (example K) of formula

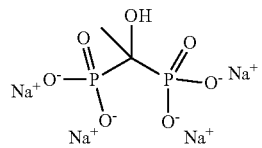

phytic acid of formula

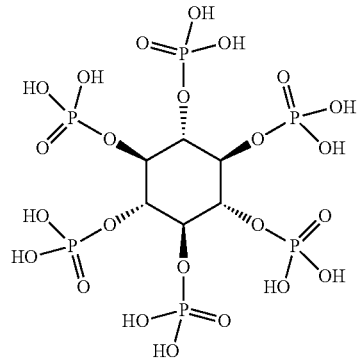 [SMILES: O=P(O)(O)O[C@H]1[C@H](OP(=O)(O)O)[C@@H](OP(=O)(O)O)[C@H](OP(=O)(O)O)[C@@H](OP(=O)(O)O)[C@@H]1OP(=O)(O)O]

and mixtures thereof.

Preferably, the polyphosphorus derivatives are chosen from inorganic polyphosphates, preferably chosen from: optionally hydrated alkali metal pyrophosphates, preferably chosen from sodium pyrophosphate, potassium pyrophosphate, sodium pyrophosphate decahydrate; and polymetaphosphates, such as sodium hexametaphosphate, sodium trimetaphosphate; sodium polyphosphates such as sodium tripolyphosphate, and mixtures thereof. Sodium and/or potassium is preferably used as alkali metal.

According to another embodiment, the organic polyphosphorus derivatives are chosen from polyphosphoric acids and/or salts thereof, such as phytic acid, polyphosphonic acids and/or salts thereof, such as EDTMP, DETMP, ATMP, HEDP, DTPMP, and mixtures thereof.

Preferably, the polyphosphorus derivative(s) (c) as defined previously represent a total content ranging from 0.5% to 20% by weight relative to the weight of the composition containing them, more particularly from 0.55% to 15% by weight and better still from 0.7% to 12% by weight.

Particularly preferably, the polyphosphorus derivative(s) (c) as defined previously are present in a total content ranging from 1% to 10% by weight relative to the weight of the composition.

Preferably, the polyphosphorus derivative(s) (c) as defined previously represent a total content ranging from 2% to 10% by weight and preferably from 2.5% to 10% by weight, relative to the total weight of the composition.

According to the invention, said polyphosphorus derivative(s) are other than said peroxygenated salt(s).

Particularly preferably, the polyphosphorus derivative(s) are not peroxygenated salts.

(d) Peroxygenated Salts

The composition according to the invention comprises (d) one or more peroxygenated salts other than the polyphosphorus derivatives described previously.

Advantageously, the peroxygenated salt(s) are chosen from persulfates and perborates of alkali metals, such as potassium or sodium; magnesium peroxide; alone or as a mixture.

According to a particularly preferred embodiment, the peroxygenated salt is not an ammonium salt.

Preferably, the composition comprises at least one persulfate as peroxygenated salt, and even more preferably at least one sodium and/or potassium persulfate.

Advantageously, the content of peroxygenated salt ranges from 0.01% to 50% by weight, preferably from 0.05% to 20% by weight and better still from 0.1% to 10% by weight relative to the weight of the composition.

Additional Oxidizing Agents:

The lightening composition according to the invention may also comprise one or more additional oxidizing agents other than the peroxygenated salts and other than the hydrogen peroxide mentioned previously.

More particularly, the additional oxidizing agent(s) may be chosen from alkali metal bromates or ferricyanides.

The composition according to the invention may also comprise one or more additional basifying agents other than the carbonate(s) (b) as defined previously, and other than the polyphosphorus derivative(s) (c) as defined previously.

Additional Basifying Agent

The additional basifying agent may be mineral or organic. It may be chosen from i) alkanolamines such as monoethanolamine, diethanolamine, triethanolamine and derivatives thereof, ii) oxyethylenated and/or oxypropylenated ethylenediamines, iii) mineral or organic hydroxides, iv) alkali metal silicates such as sodium metasilicates, v) amino acids, preferably basic amino acids such as arginine, lysine, ornithine, citrulline and histidine, and vi) the compounds of formula (II') below:

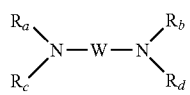

(II)

in which:
W is a divalent ($C_1$-$C_8$)alkylene group, preferably a propylene group, optionally substituted especially with a hydroxyl group or a $C_1$-$C_4$ alkyl radical;
$R_a$, $R_b$, $R_c$ and $R_d$, which may be identical or different, represent a hydrogen atom or a $C_1$-$C_4$ alkyl or $C_1$-$C_4$ hydroxyalkyl radical;
vii) and mixtures thereof.

The mineral or organic hydroxides are preferably chosen from i) hydroxides of an alkali metal, ii) hydroxides of an alkaline-earth metal, for instance sodium hydroxide or potassium hydroxide, iii) hydroxides of a transition metal, such as hydroxides of metals from groups III, IV, V and VI, iv) hydroxides of lanthanides or actinides. When they are present, the additional basifying agent(s) as defined previously preferably represent from 0.001% to 10% by weight and more particularly from 0.005% to 8% relative to the total weight of the composition(s) containing them.

According to an advantageous embodiment of the invention, the composition according to the invention does not comprise any ammonia or any ammonia-generating compound, such as ammonium salts.

According to a particularly preferred embodiment, the composition does not comprise any ammonium salts. Thus, preferably, the additional alkaline agent is not chosen from ammonia or ammonium salts.

According to an advantageous embodiment of the invention, the lightening composition according to the invention does not comprise any organic amines such as alkanolamines and in particular such as monoethanolamine.

Preferably, the composition according to the invention does not comprise any additional amino alkaline agent, in particular no ammonia or organic amine.

The composition according to the invention may also comprise one or more acidifying agents other than the polyphosphorus derivatives (c) as described previously.

Among the acidifying agents, examples that may be mentioned include mineral acids, for instance hydrochloric acid, (ortho)phosphoric acid, boric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

These acidifying agents may especially be used to adjust the pH of the composition according to the invention.

pH of the Composition

The lightening composition according to the invention preferably has a pH of less than or equal to 10, preferably less than or equal to 9.7, preferably less than or equal to 9.5.

Preferably, the composition according to the invention has a pH ranging from 6 to 10, preferably from 6 to 9.7, preferably from 6 to 9.5.

Preferably, the pH of the composition according to the invention ranges from 7 to 9.5.

In particular, it is observed that, relative to the existing lightening compositions, the compositions according to the invention make it possible to obtain a good or a better level of lightening, while at the same time having a substantially lower pH (i.e. closer to 7).

Fatty Substances

According to one embodiment, the composition according to the invention may comprise one or more fatty substances.

For the purposes of the present invention, the term "fatty substance" means an organic compound that is insoluble in water at ordinary room temperature (20-25° C.) and at atmospheric pressure (760 mmHg, i.e. 1.013×10⁵ Pa), with a solubility in water of less than 5%, preferably less than 1% and even more preferentially less than 0.1%. The fatty substances generally have in their structure a hydrocarbon-based chain comprising at least 6 carbon atoms. In addition, the fatty substances are generally soluble in organic solvents under the same temperature and pressure conditions, for instance chloroform, ethanol, benzene, liquid petroleum jelly or decamethylcyclopentasiloxane.

The fatty substances are, moreover, non-(poly)oxyalkylenated and non-(poly)glycerolated. In other words, the fatty substances do not comprise in their structure a (poly)ethylene oxide or (poly)glycerol or (poly)propylene glycol unit.

The fatty substance(s) may be chosen from solid fatty substances and/or liquid fatty substances (also called "oil"), and mixtures thereof.

The term "oil" means a "fatty substance" which is liquid, i.e. which is capable of flowing under the action of its own weight at room temperature (25° C.) and at atmospheric pressure (760 mmHg, i.e. 1,013×10⁵ Pa). Preferably, the viscosity at a temperature of 25° C. and at a shear rate of 1 s⁻¹ of the oil is between 10⁻³ Pa·s and 2 Pa·s. It may be measured using a Thermo Haake RS600 rheometer with cone-plate geometry or an equivalent machine.

For the purposes of the present invention, the term "solid fatty substance" means a fatty substance that is not liquid at room temperature (20-25° C.) and atmospheric pressure (760 mmHg, i.e. 1.013×10⁵ Pa), in particular a solid compound or a compound having a viscosity of greater than 2 Pa·s at a shear rate of 1 s$^{-1}$ under the conditions mentioned above.

The solid fatty substances used in the composition according to the invention have a melting point above room temperature, preferably a melting point greater than or equal to 40° C., preferentially ranging from 46 to 95° C.

In particular, the fatty substance may be chosen from hydrocarbon-based fatty substances, silicone fatty substances and/or fluoro fatty substances.

The term "hydrocarbon-based fatty substance" means a fatty substance formed essentially of, or even constituted of, carbon and hydrogen atoms, and optionally of oxygen or nitrogen atoms, and not comprising any silicon or fluorine atoms. It may contain alcohol, ester, ether, carboxylic acid, amine and/or amide groups.

The hydrocarbon-based fatty substance may be chosen in particular from hydrocarbons, fatty substances of animal origin, fatty substances of plant origin, fatty alcohols, fatty esters and fatty ethers.

According to a first embodiment, the fatty substance may be a silicone fatty substance.

The term "silicone fatty substance" means a fatty substance containing at least one silicon atom. The term "non-silicone fatty substance" means a fatty substance not containing any silicon (Si) atoms.

According to one embodiment, the silicone fatty substance may be a liquid silicone oil (also known as silicone oil or liquid silicone). The term "liquid silicone" means an organopolysiloxane that is liquid at ordinary temperature (25° C.) and at atmospheric pressure (760 mmHg; i.e. 1.013×10$^5$ Pa).

Preferably, the silicone is chosen from liquid polydialkylsiloxanes, in particular liquid polydimethylsiloxanes (PDMSs), and liquid polyorganosiloxanes comprising at least one aryl group.

The polydialkylsiloxanes are chosen in particular from polydimethylsiloxanes comprising trimethylsilyl end groups, and polydimethylsiloxanes comprising dimethylsilanol end groups, known under the name dimethiconol (CTFA). The polyorganosiloxanes comprising aryl groups are chosen in particular from polydiarylsiloxanes, in particular polydiphenylsiloxanes, and poly alkylarylsiloxanes.

Organopolysiloxanes are defined in greater detail in the book of Walter Noll, *Chemistry and Technology of Silicones* (1968), Academic Press. They may be volatile or non-volatile.

When they are volatile, the silicones are more particularly chosen from those with a boiling point of between 60° C. and 260° C., and even more particularly from:

(i) cyclic polydialkylsiloxanes comprising from 3 to 7 and preferably from 4 to 5 silicon atoms. These are, for example, octamethylcyclotetrasiloxane sold in particular under the name Volatile Silicone® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Mention may also be made of cyclocopolymers of the dimethylsiloxane/methylalkylsiloxane type, such as VOLATILE SILICONE® FZ 3109 sold by Union Carbide, having the formula:

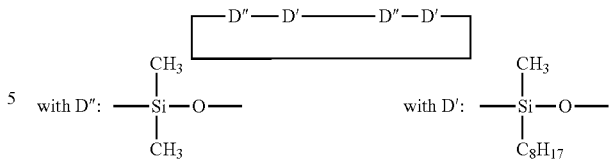

with D": —Si(CH₃)(CH₃)—O—    with D': —Si(CH₃)(C₈H₁₇)—O—

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to 5×10$^{-6}$ m$^2$/s at 25° C. An example is decamethyltetrasiloxane sold in particular under the name SH 200 by the company Toray Silicone. Silicones belonging to this category are also described in the article of Todd & Byers, *Volatile Silicone Fluids for Cosmetics*, Cosmetics and Toiletries, Vol. 91, January 76, pp. 27-32.

Non-volatile polydialkylsiloxanes, polydialkylsiloxane gums and resins, polyorganosiloxanes modified with the above organofunctional groups, and mixtures thereof, are preferably used.

These silicones are more particularly chosen from polydialkylsiloxanes, among which mention may be made mainly of polydimethylsiloxanes bearing trimethylsilyl end groups. The viscosity of the silicones is measured at 25° C. according to ASTM Standard 445 Appendix C.

Among these polydialkylsiloxanes, mention may be made, in a non-limiting manner, of the following commercial products:

the SILBIONE® oils of the 47 and 70 047 series or the MIRASIL® oils sold by Rhodia, for instance the oil 70 047 V 500 000;

the oils of the MIRASIL® series sold by Rhodia;

the oils of the 200 series from the company Dow Corning, such as DC200 with a viscosity of 60 000 mm$^2$/s;

the VISCASIL® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names ABIL WAX® 9800 and 9801 by the company Goldschmidt, which are polydi(C$_1$-C$_{20}$)alkylsiloxanes.

The silicone gums that may be used in accordance with the invention are especially polydialkylsiloxanes and preferably polydimethylsiloxanes with high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Preferably, the fatty substances that may be used in the composition according to the invention are non-silicone fatty substances, i.e. a fatty substance not containing any silicon (Si) atoms.

According to a second embodiment, the fatty substance may be a fluoro fatty substance. The term "fluoro fatty substance" means a fatty substance containing at least one fluorine atom.

In particular, fluoro fatty substances that may be mentioned include fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethylperfluoromorpholine sold under the name PF 5052® by the company 3M.

According to a preferred third embodiment, the fatty substance is a hydrocarbon-based fatty substance as defined above. In particular, preferably, the hydrocarbon-based fatty substance(s) are chosen from hydrocarbon-based oils and hydrocarbon-based solid fatty substances, and mixtures thereof, preferably chosen from hydrocarbon-based oils.

Preferably, the fatty substance(s), which are preferably hydrocarbon-based, are advantageously chosen from linear, branched, optionally cyclic, $C_6$-$C_{16}$ alkanes, such as hexane, dodecane, isoparaffins such as isohexadecane, isodecane, isododecane, and mixtures thereof, hydrocarbons containing more than 16 carbon atoms, preferably liquid paraffins, petroleum jelly, liquid petroleum jelly, polydecenes, and hydrogenated polyisobutene such as PARLEAM®, and mixtures thereof, liquid fatty alcohols such as octyldodecanol, fatty acids, and liquid esters of fatty acids and/or of fatty alcohols, or mixtures thereof.

According to a first preferred variant of the invention, the fatty substance is an oil, preferably a hydrocarbon-based oil.

Preferably, the hydrocarbon-based oils are chosen from:
halogenated or non-halogenated, linear or branched hydrocarbons, of mineral or synthetic origin, containing less than 16 carbon atoms, in particular containing between 6 and 15 carbon atoms, for instance hexane, cyclohexane, undecane, dodecane, isodecane, isohexadecane or tridecane, or containing more than 16 carbon atoms, such as liquid petroleum jelly, liquid paraffin, polydecenes of formula $C_{10n}H_{[(20n)+2]}$ in which n ranges from 3 to 9 and preferably from 3 to 7, polybutenes, hydrogenated polybutenes, polyisobutene, hydrogenated polyisobutenes such as PARLEAM®, and mixtures thereof, unsaturated or branched liquid fatty alcohols containing from 6 to 30 carbon atoms, such as those of formula $C_nH_{2n+1}OH$ with n being an integer between 6 and 20 inclusive. Mention may be made especially of oleyl alcohol, linolenyl alcohol, linoleyl alcohol, ricinoleyl alcohol, undecylenyl alcohol, isostearyl alcohol and octyldodecanol;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL®

810, 812 and 818 by the company Dynamit Nobel, jojoba oil and shea butter oil; and liquid esters other than triglycerides.

These esters are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the invention are derived is branched.

Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isodecyl neopentanoate and isostearyl neopentanoate.

Esters of $C_4$-$C_{22}$ dicarboxylic or tricarboxylic acids and of $C_1$-$C_{22}$ alcohols and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may be made especially of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, propylene glycol dicaprylate, butyl stearate, isobutyl stearate; dioctyl malate, hexyl laurate, 2-hexyldecyl laurate, isononyl isononanoate or cetyl octanoate.

The composition may also comprise, as liquid fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

The hydrocarbon-based oils are preferably chosen from the polydecenes of formula $C_{10n}H_{[(20n)+2]}$ in which n ranges from 3 to 9 and preferably from 3 to 7, fatty alcohols, esters and in particular esters of fatty alcohols or of fatty acids, sugar esters or diesters of $C_{12}$-$C_{24}$ fatty acids, cyclic esters, cyclic ethers, hydrocarbon-based oils, mineral oils, plant oils or animal oils, or mixtures thereof.

Preferably, the liquid fatty substance(s) are chosen from polydecenes, liquid petroleum jelly, liquid paraffin, isododecane, fatty alcohols such as octyldodecanol or isostearyl alcohol, and liquid esters of fatty alcohols or of fatty acids, and mixtures thereof.

Even more preferentially, the liquid fatty substances are chosen from liquid petroleum jelly, isododecane and octyldodecanol, and mixtures thereof.

Preferably, the substance(s) that are liquid at room temperature, which are preferably hydrocarbon-based, are present in the composition according to the invention in a total content ranging from 5% to 80% by weight, more preferentially from 10% to 80% by weight, preferably from 10% to 75% by weight, better still from 20% to 70% by weight, even more advantageously from 25% to 70% and preferentially from 25% to 60% by weight relative to the total weight of the composition.

According to a second variant of the invention, the hydrocarbon-based fatty substance is solid. The composition according to the invention thus comprises one or more solid, hydrocarbon-based fatty substances.

Preferably, the solid fatty substance(s) are chosen from fatty alcohols, and esters of fatty acids and/or of fatty alcohols, and waxes, and also mixtures thereof.

According to a preferred embodiment, the solid fatty substance(s) are hydrocarbon-based fatty substances, preferably chosen from solid fatty alcohols and/or solid esters of fatty acids and/or of fatty alcohols. Preferably, the solid hydrocarbon-based fatty substances are chosen from linear or branched, saturated or unsaturated solid fatty alcohols comprising from 14 to 30 carbon atoms and/or solid esters derived from $C_9$-$C_{26}$ fatty acids and from $C_9$-$C_{26}$ fatty alcohols.

Preferably, the solid fatty alcohols are saturated or unsaturated, and linear or branched, and comprise from 14 to 30 carbon atoms. Preferably, the fatty alcohol(s) are chosen from saturated and linear fatty alcohols comprising from 14 to 30 and preferably from 16 to 22 carbon atoms.

In addition, it is understood that the fatty alcohols do not comprise any $C_2$-$C_3$ oxyalkylene units or any glycerol units.

Preferably, the solid fatty substance(s) are chosen from cetyl alcohol, stearyl alcohol, behenyl alcohol and a mixture thereof. Use may be made, for example, of cetylstearyl alcohol.

The hydrocarbon-based solid fatty substance(s) may also be chosen from solid esters of fatty acids and/or of fatty alcohols; mention may be made especially of the solid esters derived from $C_9$-$C_{26}$ fatty acids and from $C_9$-$C_{26}$ fatty alcohols.

In particular, these esters may be chosen from octyldodecyl behenate, isocetyl behenate, cetyl lactate, stearyl octanoate, octyl octanoate, cetyl octanoate, decyl oleate, myristyl stearate, octyl palmitate, cetyl palmitate, octyl pelargonate, octyl stearate, alkyl myristates such as cetyl myristate, myristyl myristate or stearyl myristate, and hexyl stearate.

Preferably, the fatty substance(s) that are solid at room temperature, which are preferably hydrocarbon-based, are present in the composition according to the invention in a total content ranging from 0.1% to 15% by weight, preferably from 0.5% to 10% by weight and more preferentially from 1% to 8% by weight relative to the total weight of the composition.

Preferably, the fatty substance(s) are chosen from hydrocarbon-based fatty substances, more preferentially from:
  linear, branched, optionally cyclic $C_6$-$C_{16}$ alkanes, such as hexane, dodecane, isoparaffins such as isohexadecane, isodecane, and mixtures thereof,
  hydrocarbons with more than 16 carbon atoms, preferably liquid paraffins, petroleum jelly, liquid petroleum jelly, polydecenes, and hydrogenated polyisobutene such as PARLEAM®, and mixtures thereof,
  fatty alcohols, such as octyldodecanol, isostearyl alcohol, cetyl alcohol, stearyl alcohol and behenyl alcohol, and mixtures thereof,
  and mixtures thereof.

Preferably, they are chosen from hydrocarbon-based liquid fatty substances.

The composition according to the invention may comprise in total at least 10% by weight of fatty substances, which are preferably non-silicone, in particular of oils, which are preferably non-silicone, relative to the total weight of the composition of the invention.

More particularly, the composition according to the invention may comprise at least 15% by weight, better still at least 20% by weight and even better still at least 25% by weight of fatty substances, which are preferably non-silicone, in particular of oils, preferably non-silicone oils, relative to the total weight of the composition.

The composition according to the invention more particularly has a content of fatty substances, which are preferably non-silicone, in particular of oils, preferably non-silicone oils, ranging from 5% to 80% by weight, more preferentially from 10% to 80% by weight, preferably from 15% to 75% by weight, preferably from 20% to 75% by weight, better still from 25% to 70% by weight and even more advantageously from 35% to 60% by weight relative to the weight of the composition.

Surfactants:

The composition according to the present invention may comprise one or more surfactants. These surfactants may be chosen from anionic surfactants, amphoteric or zwitterionic surfactants, nonionic surfactants and cationic surfactants.

The term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $H_2PO_3$, $HPO_3^-$, $PO_3^{2-}$, $H_2PO_2$, $HPO_2^-$, $PO_2^{2-}$, $POH$ and $PO^-$.

As examples of anionic surfactants that can be used in the composition according to the invention, mention may be made of alkyl sulfates, alkyl ether sulfates, alkylamido ether sulfates, alkylaryl polyether sulfates, monoglyceride sulfates, alkyl sulfonates, alkylamide sulfonates, alkylaryl sulfonates, α-olefin sulfonates, paraffin sulfonates, alkyl sulfosuccinates, alkyl ether sulfosuccinates, alkylamide sulfosuccinates, alkyl sulfoacetates, acyl sarcosinates, acyl glutamates, alkyl sulfosuccinamates, acyl isethionates and N—($C_1$-$C_4$)alkyl N-acyl taurates, salts of alkyl monoesters of polyglycoside-polycarboxylic acids, acyl lactylates, salts of D-galactoside uronic acids, salts of alkyl ether carboxylic acids, salts of alkylaryl ether carboxylic acids, salts of alkylamido ether carboxylic acids; and the corresponding non-salified forms of all these compounds; the alkyl and acyl groups of all these compounds (unless specified otherwise) generally comprising from 6 to 24 carbon atoms and the aryl group generally denoting a phenyl group.

These compounds may be oxyethylenated and then preferably comprise from 1 to 50 ethylene oxide units.

The salts of $C_6$-$C_{24}$ alkyl monoesters of polyglycoside-polycarboxylic acids may be chosen from $C_6$-$C_{24}$ alkyl polyglycoside-citrates, $C_6$-$C_{24}$ alkyl polyglycoside-tartrates and $C_6$-$C_{24}$ alkyl polyglycoside-sulfosuccinates.

When the anionic surfactant(s) are in salt form, they may be chosen from alkali metal salts such as the sodium or potassium salt and preferably the sodium salt, ammonium salts, amine salts and in particular amino alcohol salts or alkaline-earth metal salts such as the magnesium salt.

Examples of amino alcohol salts that may especially be mentioned include the salts of mono-, di- and triethanolamine, the salts of mono-, di- or triisopropanolamine, and the salts of 2-amino-2-methyl-1-propanol, of 2-amino-2-methyl-1,3-propanediol and of tris(hydroxymethyl)aminomethane.

Alkali metal or alkaline-earth metal salts and in particular the sodium or magnesium salts are preferably used.

The anionic surfactants optionally present may be mild anionic surfactants, i.e. anionic surfactants without a sulfate function.

As regards the mild anionic surfactants, mention may be made in particular of the following compounds and salts thereof, and also mixtures thereof.

polyoxyalkylenated alkyl ether carboxylic acids;
polyoxyalkylenated alkylaryl ether carboxylic acids;
polyoxyalkylenated alkylamido ether carboxylic acids, in particular those comprising from 2 to 50 ethylene oxide groups;
alkyl-D-galactoside uronic acids;
acyl sarcosinates, acyl glutamates; and
alkyl polyglycoside carboxylic esters.

Use may be made most particularly of polyoxyalkylenated alkyl ether carboxylic acids, for instance lauryl ether carboxylic acid (4.5 EO), sold, for example, under the name AKYPO® RLM 45 CA from Kao.

The amphoteric or zwitterionic surfactant(s) that may be used in the present invention may especially be optionally quaternized secondary or tertiary aliphatic amine derivatives, in which the aliphatic group is a linear or branched chain containing from 8 to 22 carbon atoms, said amine derivatives containing at least one anionic group, for instance a carboxylate, sulfonate, sulfate, phosphate or phosphonate group.

Mention may be made in particular of $(C_5\text{-}C_{20})$alkylbetaines, sulfobetaines, $(C_5\text{-}C_{20})$alkylamido$(C_3\text{-}C_8)$alkylbetaines or $(C_5\text{-}C_{20})$alkylamido$(C_6\text{-}C_8)$-alkylsulfobetaines.

Among the optionally quaternized secondary or tertiary aliphatic amine derivatives that may be used, as defined above, mention may also be made of the compounds of respective structures $(A_1)$, $(A_2)$ and $(A_3)$ below:

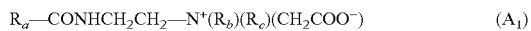
$$R_a\text{—CONHCH}_2\text{CH}_2\text{—N}^+(R_b)(R_c)(\text{CH}_2\text{COO}^-) \qquad (A_1)$$

in which:
$R_a$ represents a $C_{10}\text{-}C_{30}$ alkyl or alkenyl group derived from an acid $R_a$—COOH preferably present in hydrolysed coconut oil, or a heptyl, nonyl or undecyl group,
$R_b$ represents a β-hydroxyethyl group, and
$R_c$ represents a carboxymethyl group,
and

$$R'_a\text{—CONHCH}_2\text{CH}_2\text{—N(B)(B')} \qquad (A_2)$$

in which:
B represents —CH$_2$CH$_2$OX',
B' represents —(CH$_2$)$_z$—Y', with z=1 or 2,
X' represents the group —CH$_2$—COOH, CH$_2$—COOZ', —CH$_2$CH$_2$—COOH or —CH$_2$CH$_2$—COOZ', or a hydrogen atom,
Y' represents —COOH, —COOZ', or the group CH$_2$—CHOH—SO$_3$H or —CH$_2$—CHOH—SO$_3$Z',
Z' represents an ion derived from an alkali metal or alkaline-earth metal, such as sodium, an ammonium ion or an ion derived from an organic amine,
R'$_a$ represents a $C_{10}\text{-}C_{30}$ alkyl or alkenyl group of an acid R'$_a$—COOH preferably present in hydrolysed linseed oil or coconut oil, an alkyl group, in particular a C$_{17}$ alkyl group and its iso form, or an unsaturated C$_{17}$ group.

These compounds of formula $(A_1)$ or $(A_2)$ are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caprylamphodipropionate, lauroamphodipropionic acid, cocoamphodipropionic acid.

By way of example, mention may be made of the cocoamphodiacetate sold by the company Rhodia under the trade name MIRANOL® C2M Concentrate.

$$R_a''\text{—NHCH(Y'')—(CH}_2)_n\text{CONH(CH}_2)_{n'}\text{—N(R}_d) \atop (R_e) \qquad (A_3)$$

in which formula:
Y" represents the group —COOH, —COOZ" or —CH$_2$—CH(OH)SO$_3$H or the group —CH$_2$CH(OH)SO$_3$—Z";
$R_d$ and $R_e$, independently of each other, represent a $C_1$-$C_4$ alkyl or hydroxyalkyl radical;
Z" represents a cationic counterion derived from an alkali metal or alkaline-earth metal, such as sodium, an ammonium ion or an ion derived from an organic amine;
$R_a$" represents a $C_{10}$-$C_{30}$ alkyl or alkenyl group of an acid $R_a$"—COOH preferably present in hydrolysed linseed oil or coconut oil;
n and n' denote, independently of each other, an integer ranging from 1 to 3.

Among the compounds of formula $(A_3)$, mention may be made of the compound classified in the CTFA dictionary under the name sodium diethylaminopropyl cocoaspartamide and sold by the company Chimex under the name Chimexane HB.

Among the abovementioned amphoteric or zwitterionic surfactants, it is preferred to use $(C_{58}C_{20}$ alkyl)betaines such as cocoylbetaine, $(C_8\text{-}C_{20}$ alkyl)amido$(C_3\text{-}C_8$ alkyl)betaines such as cocoylamidopropylbetaine, and mixtures thereof. More preferentially, the amphoteric or zwitterionic surfactant(s) are chosen from cocoylamidopropylbetaine and cocoylbetaine.

The nonionic surfactant(s) in the compositions of the present invention are especially described, for example, in the Handbook of Surfactants by M. R. Porter, published by Blackie & Son (Glasgow and London), 1991, pages 116-178. They are especially chosen from fatty alcohols, fatty α-diols, fatty ($C_1$-$C_{20}$)alkylphenols and fatty acids, these compounds being ethoxylated, propoxylated or glycerolated and containing at least one fatty chain comprising, for example, from 8 to 18 carbon atoms, the number of ethylene oxide or propylene oxide groups possibly ranging especially from 1 to 200, and the number of glycerol groups possibly ranging especially from 1 to 30.

Mention may also be made of condensates of ethylene oxide and of propylene oxide with fatty alcohols, ethoxylated fatty amides preferably containing from 1 to 30 ethylene oxide units, polyglycerolated fatty amides comprising on average from 1 to 5 glycerol groups, and in particular from 1.5 to 4, ethoxylated fatty acid esters of sorbitan containing from 1 to 30 ethylene oxide units, fatty acid esters of sucrose, fatty acid esters of polyethylene glycol, ($C_6$-$C_{24}$ alkyl)polyglycosides, oxyethylenated plant oils, N—($C_6$-$C_{24}$ alkyl)glucamine derivatives, amine oxides such as ($C_{10}$-$C_{14}$ alkyl)amine oxides or N—($C_{10}$-$C_{14}$ acyl)aminopropylmorpholine oxides.

The cationic surfactant(s) that may be used in the composition according to the invention are generally chosen from optionally polyoxyalkylenated primary, secondary or tertiary fatty amine salts, quaternary ammonium salts, and mixtures thereof.

Examples of quaternary ammonium salts that may especially be mentioned include:

those corresponding to the general formula (X) below:

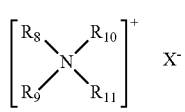

(X)

in which the groups $R_8$ to $R_{11}$, which may be identical or different, represent a linear or branched aliphatic group comprising from 1 to 30 carbon atoms or an aromatic group, such as aryl or alkylaryl, at least one of the groups $R_8$ to $R_{11}$ comprising from 8 to 30 carbon atoms and preferably from 12 to 24 carbon atoms.

The aliphatic groups may comprise heteroatoms especially such as oxygen, nitrogen, sulfur and halogens.

The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of the halides, phosphates, acetates, lactates, ($C_1$-$C_4$)alkyl sulfates and ($C_1$-$C_4$)alkyl- or ($C_1$-$C_4$)alkylarylsulfonates.

Among the quaternary ammonium salts of formula (X), preference is given, firstly, to tetraalkylammonium chlorides, for instance dialkyldimethylammonium or alkyltrimethylammonium chlorides in which the alkyl group comprises from about 12 to 22 carbon atoms, in particular behenyltrimethylammonium chloride, distearyldimethylammonium chloride, cetyltrimethylammonium chloride or benzyldimethylstearylammonium chloride, or else, secondly, to distearoylethylhydroxyethylmethylammonium methosulfate, dipalmitoylethylhydroxyethylammonium methosulfate or distearoylethylhydroxyethylammonium methosulfate, or else, finally, to palmitylamidopropyltrimethylammonium chloride or stearamidopropyldimethyl(myristyl acetate)ammonium chloride, sold under the name CERAPHYL® 70 by the company Van Dyk;

quaternary ammonium salts of imidazoline, for instance those of formula (XI) below:

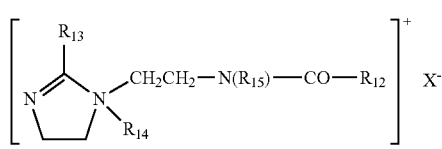

(XI)

in which $R_{12}$ represents an alkenyl or alkyl group comprising from 8 to 30 carbon atoms, for example derived from tallow fatty acids, $R_{13}$ represents a hydrogen atom, a $C_1$-$C_4$ alkyl group or an alkenyl or alkyl group comprising from 8 to 30 carbon atoms, $R_{14}$ represents a $C_1$-$C_4$ alkyl group, $R_{15}$ represents a hydrogen atom, a $C_1$-$C_4$ alkyl group, $X^-$ is an anion chosen from the group of halides, phosphates, acetates, lactates, ($C_1$-$C_4$)alkyl sulfates and ($C_1$-$C_4$)alkylsulfonates or ($C_1$-$C_4$)alkylarylsulfonates.

Preferably, $R_{12}$ and $R_{13}$ denote a mixture of alkenyl or alkyl groups comprising from 12 to 21 carbon atoms, for example derived from tallow fatty acids, $R_{14}$ denotes a methyl group and $R_{15}$ denotes a hydrogen atom. Such a product is sold, for example, under the name REWOQUAT® W 75 by the company Rewo.

quaternary diammonium or triammonium salts, particularly of formula (XII) below:

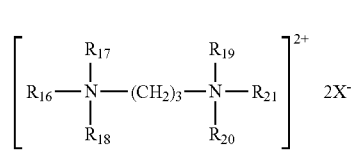

(XII)

in which $R_{16}$ denotes an alkyl group comprising approximately from 16 to 30 carbon atoms, which is optionally hydroxylated and/or interrupted with one or more oxygen atoms, $R_{17}$ is chosen from hydrogen, an alkyl group comprising from 1 to 4 carbon atoms or a group —$(CH_2)_3$—$N^+$ ($R_{16a}$)($R_{17a}$)($R_{18a}$), $R_{16a}$, $R_{17a}$, $R_{18a}$, $R_{18}$, $R_{19}$, $R_{20}$ and $R_{21}$, which may be identical or different, are chosen from hydrogen or an alkyl group comprising from 1 to 4 carbon atoms, and $X^-$ is an anion chosen from the group of halides, acetates, phosphates, nitrates, ($C_1$-$C_4$)alkyl sulfates, ($C_1$-$C_4$)alkyl- or ($C_1$-$C_4$)alkylarylsulfonates, in particular methyl sulfate and ethyl sulfate.

Such compounds are, for example, Finquat CT-P, available from Finetex (Quaternium 89), and Finquat CT, available from Finetex (Quaternium 75);

quaternary ammonium salts comprising one or more ester functions, such as those of formula (XIII) below:

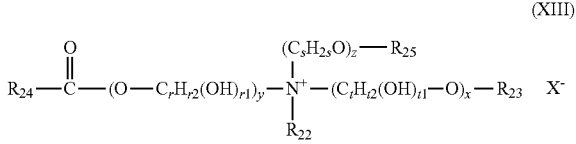

(XIII)

in which:

$R_{22}$ is chosen from $C_1$-$C_6$ alkyl groups and $C_1$-$C_6$ hydroxyalkyl or dihydroxyalkyl groups, $R_{23}$ is chosen from:

the group

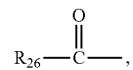

saturated or unsaturated, linear or branched $C_1$-$C_{22}$ hydrocarbon-based groups $R_{27}$,
a hydrogen atom,
$R_{25}$ is chosen from:
the group

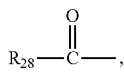

saturated or unsaturated, linear or branched $C_1$-$C_6$ hydrocarbon-based groups $R_{29}$,
a hydrogen atom,
$R_{24}$, $R_{26}$ and $R_{28}$, which may be identical or different, are chosen from saturated or unsaturated, linear or branched $C_7$-$C_{21}$ hydrocarbon-based groups;
r, s and t, which may be identical or different, are integers ranging from 2 to 6,
r1 and t1, which may be identical or different, are equal to 0 or 1,
r2+r1=2 r and t1+t2=2 t,
y is an integer ranging from 1 to 10,
x and z, which may be identical or different, are integers ranging from 0 to 10,
$X^-$ is a simple or complex, organic or inorganic anion,
with the proviso that the sum x+y+z is from 1 to 15, that when x is 0 then $R_{23}$ denotes $R_{27}$, and that when z is 0 then $R_{25}$ denotes $R_{29}$.

The alkyl groups $R_{22}$ may be linear or branched, and more particularly linear.

Preferably, $R_{22}$ denotes a methyl, ethyl, hydroxyethyl or dihydroxypropyl group, and more particularly a methyl or ethyl group.

Advantageously, the sum x+y+z ranges from 1 to 10.

When $R_{23}$ is a hydrocarbon-based group $R_{27}$, it may be long and contain from 12 to 22 carbon atoms, or may be short and contain from 1 to 3 carbon atoms.

When $R_{25}$ is a hydrocarbon-based group $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based groups, and more particularly from linear or branched, saturated or unsaturated $C_{11}$-$C_{21}$ alkyl and alkenyl groups.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide, preferably chloride, bromide or iodide, a ($C_1$-$C_4$)alkyl sulfate, or a ($C_1$-$C_4$) alkylsulfonate or ($C_1$-$C_4$)alkylarylsulfonate. However, use may be made of methanesulfonate, phosphate, nitrate, tosylate, an anion derived from an organic acid, such as acetate or lactate, or any other anion that is compatible with the ammonium bearing an ester function.

The anion $X^-$ is even more particularly chloride, methyl sulfate or ethyl sulfate.

Use is made more particularly, in the composition according to the invention, of the ammonium salts of formula (XIII) in which:
$R_{22}$ denotes a methyl or ethyl group,
x and y are equal to 1,
z is equal to 0 or 1,
r, s and t are equal to 2,
$R_{23}$ is chosen from:
the group

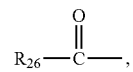

methyl, ethyl or $C_{14}$-$C_{22}$ hydrocarbon-based groups,
a hydrogen atom,
$R_{25}$ is chosen from:
the group

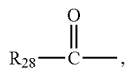

a hydrogen atom,
$R_{24}$, $R_{26}$ and $R_{28}$, which may be identical or different, are chosen from linear or branched, saturated or unsaturated $C_{13}$-$C_{17}$ hydrocarbon-based groups, and preferably from linear or branched, saturated or unsaturated $C_{13}$-$C_{17}$ alkyl and alkenyl groups.

Advantageously, the hydrocarbon-based groups are linear.

Among the compounds of formula (XIII), examples that may be mentioned include salts, especially the chloride or methyl sulfate, of diacyloxyethyldimethylammonium, diacyloxyethylhydroxyethylmethylammonium, monoacyloxyethyldihydroxyethylmethylammonium, triacyloxyethylmethylammonium or monoacyloxyethylhydroxyethyldimethylammonium, and mixtures thereof. The acyl groups preferably contain 14 to 18 carbon atoms and are obtained more particularly from a plant oil such as palm oil or sunflower oil. When the compound contains several acyl groups, these groups may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization by means of an alkylating agent such as an alkyl halide, preferably a methyl or ethyl halide, a dialkyl sulfate, preferably a dimethyl or diethyl sulfate, methyl methanesulfonate, methyl para-toluenesulfonate, glycol chlorohydrin or glycerol chlorohydrin.

Such compounds are sold, for example, under the names DEHYQUART® by the company Henkel, STEPANQUAT® by the company Stepan, NOXAMIUM® by the company Ceca or REWOQUAT® WE 18 by the company Rewo-Witco.

The composition according to the invention may contain, for example, a mixture of quaternary ammonium monoester, diester and triester salts with a weight majority of diester salts.

Use may also be made of the ammonium salts containing at least one ester function that are described in U.S. Pat. Nos. 4,874,554 and 4,137,180.

Use may also be made of behenoylhydroxypropyltrimethylammonium chloride, for example, sold by the company Kao under the name Quartamin BTC 131.

Preferably, the ammonium salts containing at least one ester function contain two ester functions.

Among the cationic surfactants, it is more particularly preferred to choose cetyltrimethylammonium, behenyltrimethylammonium and dipalmitoylethylhydroxyethylmethylammonium salts, and mixtures thereof, and more particularly behenyltrimethylammonium chloride, cetyltrimethylammonium chloride, and dipalmitoylethylhydroxyethylammonium methosulfate, and mixtures thereof.

Preferably, the surfactant(s) are chosen from anionic and/or nonionic surfactants, preferably nonionic surfactants.

When the composition comprises one or more surfactants, their content may preferably range from 0.05% to 20% by weight, more preferentially from 0.1% to 10% by weight and better still from 0.5% to 5% by weight relative to the total weight of the composition.

Liquid Organic Solvents

According to one embodiment of the invention, the composition according to the invention comprises one or more liquid organic solvents, preferably chosen from liquid organic compounds with a Hansen solubility parameter SH of greater than 0 and less than 16 MPa$^{1/2}$.

In the context of the present invention, such a compound is also known as a "hydrotropic compound".

For the purposes of the present invention, the term "hydrotropic compound" means a compound that is capable of increasing the solubility of hydrophobic compounds in aqueous phases.

Said liquid compounds more preferably have a Hansen solubility parameter SH of between 5 and 15.8 MPa1/2, even more preferentially between 8 and 15.8 MPa1/2 and better still between 8 and 15 MPa1/2.

These compounds are liquid at a temperature of 25° C. and at atmospheric pressure (760 mmHg; i.e. 1.013×10$^5$ Pa).

The compound(s) with a Hansen solubility parameter SH value as defined previously are, for example, described in the reference publication of Charles M. Hansen, *Hansen solubility parameters: A User's Handbook*, CRC Press, 2000, pages 167 to 185, or in the publication Barton, Allan F M, *Handbook of Solubility Parameters and Other Cohesion Parameters*, Second Edition, CRC Press, pages 95 to 121 and pages 177 to 185.

This value of the solubility parameter SH is related to the formation of hydrogen bonds. It may be recalled that there exist three major types of interactions in organic compounds: non-polar interactions, permanent dipole-dipole interactions and interactions of hydrogen bond type, the latter interactions forming the subject of the parameter defining the hydrotropic compound present in the composition employed in accordance with the invention.

In particular, the reference publication of Barton, Allan F M, *Handbook of Solubility Parameters and Other Cohesion Parameters*, CRC Press, pages 95 to 121 and pages 177 to 185, gives the equation $\delta H=(\Sigma-zUh/V)^{1/2}$, in which zUh (in J·mol$^{-1}$) describes the contributions of the functional group considered in the solubility parameters associated with the hydrogen bonds (values in Table 14, page 183), this parameter zUh also being described in the book The relation between surface tension and solubility parameter in liquids, Bagda, E, Farbe Lack, 84, 212, 1978; and V is the volume of the molecule.

It should be noted that the value of the solubility parameter SH is usually given for a temperature of 25° C. and at atmospheric pressure (760 mmHg, i.e. 1.013×10$^5$ Pa).

In particular, the liquid organic compounds with a Hansen solubility parameter SH value of greater than 0 and less than 16 MPa1/2 are nonionic compounds.

Preferably, said liquid organic solvent(s) are chosen from alcohol ethers, aliphatic esters, aliphatic ethers, aromatic ethers, alkanols bearing aryl substituents, lactones and mixtures thereof.

Said liquid organic solvent(s) may preferably be chosen from:
  alcohol ethers, in particular C1-C4 ethers of C5-C30 alcohols, which are preferably saturated, linear or branched, optionally interrupted with one or more non-adjacent ether functions;
  aliphatic esters of C1-C4 carboxylic acids and of C3-C10 monoalcohols or polyhydroxylated alcohols, interrupted with one or more non-adjacent ether functions;
  aromatic ethers, in particular C6-C10 aromatic ethers, of a C1-C6 alkyl optionally bearing a hydroxyl group;
  (C6-C10)aryl(C1-C6)alkyl ethers, of a C1-C6 alkyl optionally bearing a hydroxyl group;
  alkanols bearing an aryl substituent, preferably for which the aryl part is a C6-C10 aryl part, advantageously a C6 aryl part, and the alkyl part of the alkanol is a C1-C4 alkyl part, this alkyl part possibly ending or being interrupted with a heteroatom, advantageously oxygen or a hydroxyl group, preferably such as benzyl alcohol;
  lactones preferably of formula (iii), and also mixtures thereof, with:

in which R' represents a hydrogen, a linear or branched C1-C8 alkyl, a linear or branched C1-C4 hydroxyalkyl, n is equal to 1, 2 or 3, and preferably R' represents a hydrogen, a linear or branched C1-C6 alkyl or a linear or branched C1-C2 hydroxyalkyl.

A particularly advantageous example of lactones that may be mentioned is γ-butyrolactone.

Mention may also be made of certain liquid alkanols, for instance 1-pentanol.

Even more preferably, said liquid organic solvent(s) are chosen from dipropylene glycol monomethyl ether acetate, dipropylene glycol methyl ether, dipropylene glycol mono(n-butyl) ether (the INCI name of which is PPG-2 Butyl Ether), tripropylene glycol methyl ether, propylene glycol n-butyl ether, propylene glycol n-propyl ether, propylene glycol monomethyl ether, diethylene glycol monomethyl ether and monoethyl ether, 3-phenyl-1-propanol, 2-phenyl-1-propanol, benzyl alcohol, benzyloxyethanol, phenoxyethanol, and mixtures of these compounds.

The liquid organic solvent(s) are preferably chosen from propylene glycol derivatives and aromatic alcohols, and mixtures thereof, even more preferentially chosen from alkanols bearing aryl substituents and even more preferentially benzyl alcohol and/or propylene glycol n-butyl ether.

Use may be made of other organic solvents, different from the liquid organic compound(s) with a Hansen solubility parameter δH value of greater than 0 and less than 16 MPa$^{1/2}$. Examples that may be mentioned include $C_1$-$C_4$ lower alkanols such as ethanol and isopropanol; polyols and polyol ethers.

Preferably, when they are present, the liquid organic solvent(s) represent a total content ranging from 0.1% to 35% by weight, preferably from 0.1% to 20% by weight and better still from 0.5% to 10% by weight, relative to the total weight of the composition.

Direct Dyes

The composition according to the invention may optionally comprise b) one or more synthetic or natural direct dyes, chosen from cationic, anionic and nonionic species, preferably cationic or nonionic species.

Examples of suitable direct dyes that may be mentioned include azo direct dyes; (poly)methine dyes such as cyanines, hemicyanines and styryls; carbonyl dyes; azine dyes; nitro(hetero)aryl dyes; tri(hetero)arylmethane dyes; porphyrin dyes; phthalocyanine dyes and natural direct dyes, alone or in the form of mixtures.

The direct dyes are preferably cationic direct dyes. Mention may be made of the hydrazono cationic dyes of formulae (IIIa) and (III'a), the azo cationic dyes (IVa) and (IV'a) and the diazo cationic dyes (Va) below:

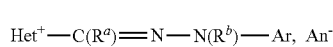 (IIIa)

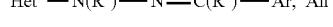 (III'a)

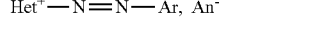 (IVa)

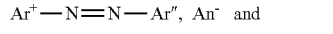 (IV'a)

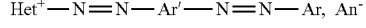 (Va)

in which formulae (IIIa), (III'a), (IVa), (IV'a) and (Va):

Het$^+$ represents a cationic heteroaryl radical, preferably bearing an endocyclic cationic charge, such as imidazolium, indolium or pyridinium, optionally substituted preferably with one or more ($C_1$-$C_8$)alkyl groups such as methyl;

Ar$^+$ represents an aryl radical, such as phenyl or naphthyl, bearing an exocyclic cationic charge, preferably ammonium, particularly tri($C_1$-$C_8$)alkylammonium such as trimethylammonium;

Ar represents an aryl group, especially phenyl, which is optionally substituted, preferably with one or more electron-donating groups such as i) optionally substituted ($C_1$-$C_8$)alkyl, ii) optionally substituted ($C_1$-$C_8$)alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or, as a variant, Ar represents a julolidine group;

Ar' represents an optionally substituted divalent (hetero)arylene group such as phenylene, particularly paraphenylene, or naphthalene, which are optionally substituted, preferably with one or more groups ($C_1$-$C_8$) alkyl, hydroxyl or ($C_1$-$C_8$)alkoxy;

Ar" represents an optionally substituted (hetero)aryl group such as phenyl or pyrazolyl, which are optionally substituted, preferably with one or more ($C_1$-$C_8$)alkyl, hydroxyl, (di)($C_1$-$C_8$)(alkyl)amino, ($C_1$-$C_8$)alkoxy or phenyl groups;

R$^a$ and R$^b$, which may be identical or different, represent a hydrogen atom or a ($C_1$-$C_8$)alkyl group, which is optionally substituted, preferably with a hydroxyl group;

or, as a variant, the substituent R$^a$ with a substituent of Het$^+$ and/or R$^b$ with a substituent of Ar and/or R$^a$ with R$^b$ form, together with the atoms that bear them, a (hetero)cycloalkyl;

particularly, R$^a$ and R$^b$ represent a hydrogen atom or a ($C_1$-$C_4$)alkyl group, which is optionally substituted with a hydroxyl group;

An$^-$ represents an anionic counterion, such as mesylate or halide.

Mention may be made in particular of azo and hydrazono cationic dyes bearing an endocyclic cationic charge of formulae (IIIa), (III'a) and (IVa) as defined previously, more particularly those of formulae (IIIa), (III'a) and (IVa) derived from the dyes described in patent applications WO 95/15144, WO 95/01772 and EP-714954.

Preferably, the cationic part is derived from the following derivatives:

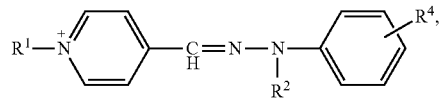 (IIIa-1)

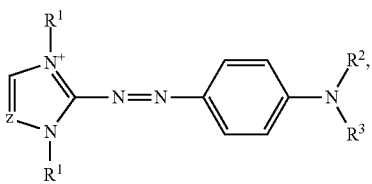 (IVa-1)

formulae (III-1) and (IV-1) with:

R$^1$ representing a ($C_1$-$C_4$)alkyl group such as methyl;

R$^2$ and R$^3$, which may be identical or different, representing a hydrogen atom or a ($C_1$-$C_4$)alkyl group, such as methyl; and R$^4$ representing a hydrogen atom or an electron-donating group such as an optionally substituted ($C_1$-$C_8$) alkyl group, an optionally substituted ($C_1$-$C_8$)alkoxy group, or a (di)($C_1$-$C_8$)(alkyl)amino group optionally substituted on the alkyl group(s) with a hydroxyl group; in particular, R$^4$ represents a hydrogen atom;

Z representing a CH group or a nitrogen atom, preferably CH,

An$^-$ representing an anionic counterion, such as mesylate or halide.

In particular, the dye of formulae (IIIa-1) and (IVa-1) is chosen from Basic Red 51, Basic Yellow 87 and Basic Orange 31 or corresponding derivatives:

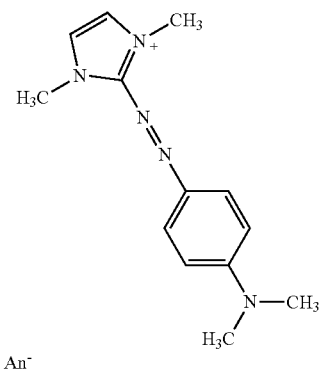

-continued

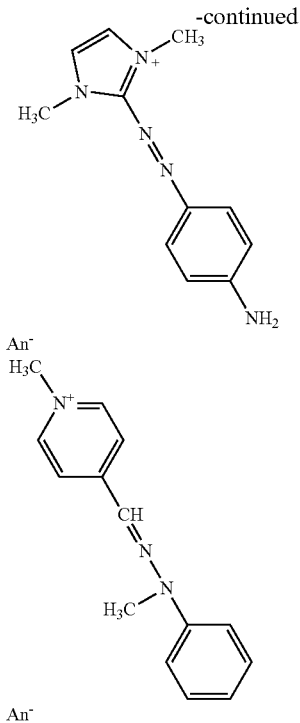

Among the natural direct dyes that may be used according to the invention, mention may be made of hennotannic acid, juglone, alizarin, purpurin, carminic acid, kermesic acid, purpurogallin, protocatechaldehyde, indigo, isatin, curcumin, spinulosin, apigenidin and orcein. Extracts or decoctions containing these natural dyes and in particular henna-based extracts or poultices may also be used.

When they are present, the direct dye(s) more particularly represent from 0.001% to 10% by weight and preferably from 0.005% to 5% by weight relative to the total weight of the composition.

According to a particular embodiment of the invention, the process is a dyeing process and the composition contains at least one direct dye as defined previously.

Medium

The cosmetically acceptable medium that is suitable for lightening keratin fibres, also known as the support, generally comprises water or a mixture of water and of at least one organic solvent as described previously or a mixture of organic solvents, to dissolve the compounds that would not be sufficiently water-soluble.

The compositions used according to the invention generally comprise water or a mixture of water and of one or more organic solvents or a mixture of organic solvents.

The composition according to the invention preferably comprises water. Preferably, the water content ranges from 5% to 90% by weight, more preferentially from 10% to 80% by weight and better still from 20% to 70% by weight relative to the total weight of the composition.

Cationic Polymers

According to an advantageous embodiment of the invention, the composition comprises one or more cationic polymers.

As cationic polymers that may be used in the compositions according to the invention, mention may be made in particular of:

(1) cyclopolymers of alkyldiallylamine or of dialkyldiallylammonium, such as the homopolymers or copolymers containing, as main constituent of the chain, units corresponding to formula (V) or (VI):

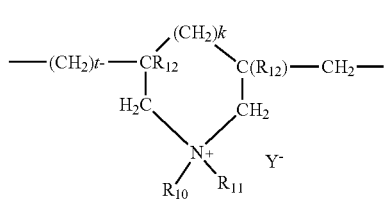

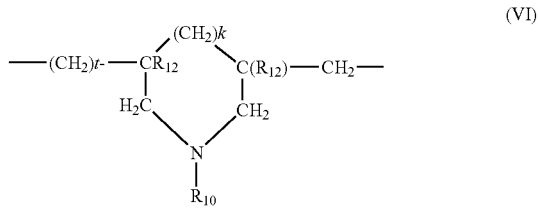

in which
k and t are equal to 0 or 1, the sum k+t being equal to 1;
$R_{12}$ denotes a hydrogen atom or a methyl radical;
$R_{10}$ and $R_{11}$, independently of each other, denote a $C_1$-$C_6$ alkyl group, a $C_1$-$C_5$ hydroxyalkyl group, a $C_1$-$C_4$ amidoalkyl group; or alternatively $R_{10}$ and $R_{11}$ may denote, together with the nitrogen atom to which they are attached, a heterocyclic group such as piperidyl or morpholinyl; $R_{10}$ and $R_{11}$, independently of each other, preferably denote a $C_1$-$C_4$ alkyl group;
$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer for example sold under the name Merquat 100 by the company Nalco. Preferably, the polymers of family (V) are chosen from dialkyldiallylammonium homopolymers.

(2) quaternary diammonium polymers comprising repeating units of formula:

in which:
$R_{13}$, $R_{14}$, $R_{15}$ and $R_{16}$, which may be identical or different, represent aliphatic, alicyclic or arylaliphatic radicals comprising from 1 to 20 carbon atoms or $C_1$-$C_{12}$ hydroxyalkyl aliphatic radicals,
or else $R_{13}$, $R_{14}$, $R_{15}$ and $R_{16}$, together or separately, form, with the nitrogen atoms to which they are attached, heterocycles optionally comprising a second non-nitrogen heteroatom;
or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group, where $R_{17}$ is an alkylene and D is a quaternary ammonium group;

A$_1$ and B$_1$ represent linear or branched, saturated or unsaturated, divalent polymethylene groups comprising from 2 to 20 carbon atoms, which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and X$^-$ denotes an anion derived from a mineral or organic acid;

it being understood that A$_1$, R$_{13}$ and R$_{15}$ can form, with the two nitrogen atoms to which they are attached, a piperazine ring;

in addition, if A$_1$ denotes a linear or branched, saturated or unsaturated alkylene or hydroxyalkylene radical, B$_1$ may also denote a group (CH$_2$)n-CO-D-OC—(CH$_2$)p- with n and p, which may be identical or different, being integers ranging from 2 to 20, and D denoting:
  a) a glycol residue of formula —O—Z—O—, in which Z denotes a linear or branched hydrocarbon-based radical, or a group corresponding to one of the following formulae: —(CH$_2$CH$_2$O)x-CH$_2$CH$_2$— and —[CH$_2$CH(CH$_3$)O]y-CH$_2$CH(CH$_3$)—, in which x and y denote an integer from 1 to 4, representing a defined and unique degree of polymerization or any number from 1 to 4 representing an average degree of polymerization;
  b) a bis-secondary diamine residue, such as a piperazine derivative;
  c) a bis-primary diamine residue of formula —NH—Y—NH—, in which Y denotes a linear or branched hydrocarbon-based radical, or else the divalent radical —CH$_2$—CH$_2$—S—S—CH$_2$—CH$_2$—;
  d) a ureylene group of formula —NH—CO—NH—.

Preferably, X$^-$ is an anion, such as chloride or bromide. These polymers have a number-average molar mass (Mn) generally of between 1000 and 100 000.

Mention may be made more particularly of cationic polymers that are constituted of repeating units corresponding to the formula:

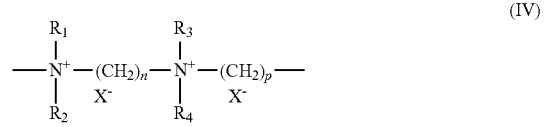

(IV)

in which R$_1$, R$_2$, R$_3$ and R$_4$, which may be identical or different, denote an alkyl or hydroxyalkyl radical containing from 1 to 4 carbon atoms, n and p are integers ranging from 2 to 20, and X$^-$ is an anion derived from a mineral or organic acid.

A particularly preferred compound of formula (IV) is the one for which R$_1$, R$_2$, R$_3$ and R$_4$ represent a methyl radical and n=3, p=6 and X=Cl, known as Hexadimethrine chloride according to the INCI (CTFA) nomenclature.

Preferably, the cationic polymer(s) are chosen from dialkyldiallylammonium homopolymers, in particular homopolymers of dimethyldiallylammonium salts, polymers constituted of repeating units corresponding to formula (IV) above, in particular poly(dimethyliminio)-1,3-propanediyl (dimethyliminio)-1,6-hexanediyl dichloride, the INCI name of which is hexadimethrine chloride, and mixtures thereof.

When they are present, the concentration of cationic polymers in the composition according to the present invention may range from 0.01% to 10% by weight relative to the weight of the composition, preferably from 0.10% to 5% relative to the weight of the composition, and even more advantageously from 0.2% to 3% by weight relative to the weight of the composition.

Other Additives

The composition according to the invention may also contain various adjuvants conventionally used in hair lightening compositions, such as anionic, cationic, nonionic, amphoteric or zwitterionic polymers or mixtures thereof; mineral thickeners, and in particular fillers such as clays or talc; organic thickeners with, in particular, anionic, cationic, nonionic and amphoteric polymeric associative thickeners; antioxidants; penetrants; sequestrants; fragrances; dispersants; film-forming agents; ceramides; preserving agents; opacifiers.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these possible additional compound(s) such that the advantageous properties intrinsically associated with the composition(s) that are useful in the lightening process in accordance with the invention are not, or are not substantially, adversely affected by the envisaged addition(s).

The composition may especially comprise one or more thickeners. In particular, the thickeners may be mineral thickeners chosen from organophilic clays and fumed silicas, or mixtures thereof.

The organophilic clay may be chosen from montmorillonite, bentonite, hectorite, attapulgite and sepiolite, and mixtures thereof. The clay is preferably a bentonite or a hectorite.

These clays may be modified with a chemical compound chosen from quaternary amines, tertiary amines, amine acetates, imidazolines, amine soaps, fatty sulfates, alkylarylsulfonates and amine oxides, and mixtures thereof.

Mention may be made, as organophilic clays, of quaternium-18 bentonites, such as those sold under the names Bentone® 3, Bentone® 38 and Bentone® 38V by Rheox, TIXOGEL® VP by United Catalyst and CLAYTONE® 34, CLAYTONE® 40 and CLAYTONE® XL by Southern Clay; stearalkonium bentonites, such as those sold under the names BENTONE® 27 by Rheox, TIXOGEL® LG by United Catalyst and CLAYTONE® AF and CLAYTONE® APA by Southern Clay; and quaternium-18/benzalkonium bentonites, such as those sold under the names CLAYTONE® HT and CLAYTONE® PS by Southern Clay.

The fumed silicas may be obtained by high-temperature hydrolysis of a volatile silicon compound in an oxyhydrogen flame, producing a finely divided silica. This process makes it possible in particular to obtain hydrophilic silicas bearing a large number of silanol groups at their surface. Such hydrophilic silicas are sold, for example, under the names AEROSIL 130®, AEROSIL 200®, AEROSIL 255®, AEROSIL 300® and AEROSIL 380® by Degussa and CAB-O-SIL HS-5®, CAB-O-SIL EH-5®, CAB-O-SIL LM-130®, CAB-O-SIL MS-55® and CAB-O-SIL M-5® by Cabot.

It is possible to chemically modify the surface of the silica via chemical reaction in order to reduce the number of silanol groups. It is especially possible to substitute silanol groups with hydrophobic groups: a hydrophobic silica is then obtained.

The hydrophobic groups may be:

trimethylsiloxyl groups, which are obtained in particular by treating fumed silica in the presence of hexamethyldisilazane. Silicas thus treated are known as Silica silylate according to the CTFA (6th Edition, 1995). They are sold, for example, under the references AEROSIL R812® by Degussa and CAB-O-SIL TS-530® by Cabot.

dimethylsilyloxyl or polydimethylsiloxane groups, which are obtained in particular by treating fumed silica in the presence of polydimethylsiloxane or dimethyldichlorosilane. Silicas thus treated are known as Silica dimethyl silylate according to the CTFA (6th Edition, 1995). They are sold, for example, under the references AEROSIL R972® and AEROSIL R974® by the company Degussa and CAB-O-SIL TS-610® and CAB-O-SIL TS-720® by the company Cabot.

The fumed silica preferably has a particle size that may be nanometric to micrometric, for example ranging from about 5 to 200 nm.

When it is present, the mineral thickener represents from 1% to 30% by weight relative to the weight of the composition.

The composition may also comprise one or more organic thickeners.

These thickeners may be chosen from fatty acid amides (coconut monoethanolamide or diethanolamide, oxyethylenated carboxylic acid alkyl ether monoethanolamide), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), crosslinked acrylic acid or acrylamidopropanesulfonic acid homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to a particular embodiment, the organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum or scleroglucan gum) and crosslinked acrylic acid or acrylamidopropanesulfonic acid homopolymers, and preferably from cellulose-based thickeners in particular with hydroxyethylcellulose.

The content of organic thickener(s), if they are present, usually ranges from 0.01% to 20% by weight relative to the weight of the composition, and preferably from 0.1% to 5% by weight.

The composition of the invention may be in various forms, for instance a solution, an emulsion (milk or cream) or a gel, preferably in the form of an emulsion and particularly of a direct emulsion.

Preferably, the lightening composition according to the invention comprises:
(a) hydrogen peroxide,
(b) one or more carbonates and/or one or more carbonate-generating systems,
(c) one or more polyphosphorus derivatives preferably chosen from linear or cyclic compounds comprising at least two phosphorus atoms covalently bonded together via at least one linker L comprising at least one oxygen atom and/or at least one carbon atom, in a total content of greater than or equal to 0.5% by weight, relative to the total weight of the composition,
(d) one or more peroxygenated salts,
(e) preferably, one or more surfactants,
(f) preferably, one or more fatty substances, preferably non-silicone fatty substances,
(g) preferably, one or more liquid organic solvents,
said polyphosphorus derivative(s) being different from said peroxygenated salt(s), and the pH of said composition preferably being less than or equal to 10, preferably between 6 and 10, preferably between 6 and 9.7, better still ranging from 6 to 9.5.

Preferably, the lightening composition according to the invention comprises:
(a) hydrogen peroxide,
(b) one or more carbonates and/or one or more carbonate-generating systems,
(c) one or more polyphosphorus derivatives preferably chosen from linear or cyclic compounds comprising at least two phosphorus atoms covalently bonded together via at least one linker L comprising at least one oxygen atom and/or at least one carbon atom, in a total content of greater than or equal to 0.5% by weight, relative to the total weight of the composition,
(d) one or more peroxygenated salts,
(e) preferably, one or more surfactants,
(f) preferably, one or more fatty substances in a content ranging from 5% to 40% by weight, preferably from 5% to 30% by weight and better still from 10% to 25%, relative to the weight of the composition, and
(g) preferably, one or more liquid organic solvents,
said polyphosphorus derivative(s) being different from said peroxygenated salt(s), and the pH of said composition being less than or equal to 10, preferably less than or equal to 9.7, preferably less than or equal to 9.5. Preferably, the pH of the composition according to the invention ranges from 6 to 9.7 and better still from 6 to 9.5.

Lightening Process

The lightening process according to the invention consists in applying the composition comprising at least ingredients (a) to (d) and optionally ingredients (e), and/or (f) and/or (g) as defined previously to keratin materials, preferably wet or dry keratin fibres. The composition is left in place for a time generally from 1 minute to 1 hour, preferably from 5 minutes to 30 minutes.

The temperature during the lightening process is conventionally between room temperature (between 15° C. and 25° C.) and 80° C. and preferably between room temperature and 60° C.

On conclusion of the treatment, the keratin materials, preferably human keratin fibres, are optionally rinsed with water, optionally washed with a shampoo and then rinsed with water, before being dried or left to dry.

The composition according to the invention is preferably prepared by mixing at least two compositions. Preferably, the mixing of said at least two compositions is performed extemporaneously, before application of the composition according to the invention to the keratin fibres.

In a first variant of the invention, the composition according to the invention comprising at least the ingredients (a) to (d) and optionally ingredients (e), and/or (f) and/or (g) as defined previously results from the mixing of two compositions:

a composition (A) comprising (a) hydrogen peroxide, and (d) one or more peroxygenated salts, and a composition (B) comprising (b) one or more carbonates and/or one or more carbonate-generating systems as defined previously, and (c) one or more polyphosphorus derivatives as defined previously, said polyphosphorus derivative(s) being different from said peroxygenated salt(s), such that the content of polyphosphorus derivatives (c) in the lightening composition according to the invention resulting from the mixing of compositions (A)+(B) is greater than or equal to 0.5% by weight relative to the total weight of the composition and preferably such that the pH of the composition according to the invention resulting from the mixing of compositions (A)+(B) is less than or equal to 10, preferably less than or equal to 9.7, preferably less than or equal to 9.5. Preferably, the pH of the composition ranges from 6 to 9.7 and better still from 6 to 9.5.

Preferentially, at least one of the compositions (A) or (B) is aqueous.

Even more preferentially, both the compositions (A) and (B) are aqueous.

The term "aqueous composition" means a composition comprising at least 5% water. Preferably, an aqueous composition comprises more than 10% by weight of water and even more advantageously more than 20% by weight of water.

Preferably, composition (A) is aqueous.

Compositions (A) and (B) are preferably mixed in a weight ratio (A)/(B) ranging from 0.2 to 10 and better still from 0.5 to 2.

In accordance with this embodiment, the lightening process thus consists in applying to the keratin fibres the lightening composition derived from the mixing of compositions (A) and (B) mentioned above.

In a second variant of the invention, the composition according to the invention comprising at least the ingredients (a) to (d) and optionally ingredients (e), and/or (f) and/or (g) as defined previously results from the mixing of two compositions:

a composition (A) comprising (c) one or more polyphosphorus derivatives as described previously and (a) hydrogen peroxide and (d) one or more peroxygenated salts, said polyphosphorus derivative(s) being different from said peroxygenated salt(s), and a composition (B) comprising (b) one or more carbonates and/or one or more carbonate-generating systems as defined previously, and (c) one or more polyphosphorus derivatives as defined previously, such that the content of polyphosphorus derivatives (c) in the lightening composition according to the invention resulting from the mixing of compositions (A)+(B) is greater than or equal to 0.5% by weight relative to the total weight of the composition and such that the pH of the composition according to the invention resulting from the mixing of compositions (A)+(B) is preferably less than or equal to 10, preferably less than or equal to 9.7, preferably less than or equal to 9.5. Preferably, the pH of the composition ranges from 6 to 9.7 and better still from 6 to 9.5.

In a third variant of the invention, the composition according to the invention comprising at least the ingredients (a) to (d) and optionally ingredients (e), and/or (f) and/or (g) as defined previously results from the mixing of three compositions:

a composition (A) comprising (a) hydrogen peroxide, a composition (B) comprising (d) one or more peroxygenated salts, and a composition (C) comprising (b) one or more carbonates and/or one or more carbonate-generating systems as defined previously, and (c) one or more polyphosphorus derivatives as defined previously, said polyphosphorus derivative(s) being different from said peroxygenated salt(s), such that the content of polyphosphorus derivatives (c) in the lightening composition according to the invention resulting from the mixing of compositions (A)+(B)+(C) is greater than or equal to 0.5% by weight relative to the total weight of the composition and such that the pH of the composition according to the invention resulting from the mixing of compositions (A)+(B)+(C) is less than or equal to 10, preferably less than or equal to 9.7, preferably less than or equal to 9.5. Preferably, the pH of the composition ranges from 6 to 9.7 and better still from 6 to 9.5.

Device

Finally, the invention relates to a multi-compartment device comprising at least a first compartment containing composition (A) as described above and at least a second compartment containing composition (B) as described above, and optionally a third compartment comprising composition (C) as described previously, the compositions of the compartments being intended to be mixed before application.

The content of polyphosphorus derivative(s) in the formulation derived from the mixing of (A)+(B) or (A)+(B)+(C) is greater than or equal to 0.5% by weight relative to the weight of the formulation derived from the mixing of the compositions of the various compartments and the pH is less than or equal to 10, preferably less than or equal to 9.7, preferably less than or equal to 9.5. Preferably, the pH of the composition ranges from 6 to 9.7 and better still from 6 to 9.5.

The examples that follow serve to illustrate the invention without, however, being limiting in nature.

In these examples, the colour of the locks was evaluated in the CIE L*a*b* system, using a Minolta Spectrophotometer CM2600D colorimeter.

In this L*a*b* system, the three parameters denote, respectively, the colour intensity (L*), the green/red colour axis (a*) and the blue/yellow colour axis (b*). The higher the value of L*, the lighter the colour. The higher the value of a*, the redder the colour and the higher the value of b*, the yellower the colour.

The variation or extent of the lightening between untreated locks of hair and locks of hair after treatment is defined by the parameter DE* and is calculated according to the following equation:

$$DE^* = \sqrt{(L^* - L_o^*)^2 + (a^* - a_o^*)^2 + (b^* - b_o^*)^2} \quad (i)$$

In this equation, the parameters L*, a* and b* represent the values measured on locks of hair after lightening and the parameters $L_o^*$, $a_o^*$ and $b_o^*$ represent the values measured on untreated locks of hair. The higher the DE* value, the better the lightening of the keratin fibres.

EXAMPLES

Example 1

The following compositions were prepared from the following ingredients in the following proportions, indicated in grams:

|  | compo A comparative | compo B invention |
|---|---|---|
| Sodium carbonate | 1.9 | 1.9 |
| Potassium pyrophosphate | — | 5.7 |
| Potassium persulfate | 4.8 | 4.8 |
| Water | qs 100 | qs 100 |
| pH agent (1N hydrochloric acid or pyrophosphoric acid) | pH 10.0 | pH 10.0 |

The lightening compositions are made by mixing:
87.5 grams of each of the compositions A or
and 12.5 grams of aqueous hydrogen peroxide solution (50% concentration).

The mixtures thus obtained are applied to locks of natural pigmented Caucasian hair with a tone depth of 4 (TD4).

The "mixture/lock" bath ratio is, respectively, 10/1 (g/g).

The leave-on time is 1 hour, on a hotplate set at 40° C. On conclusion of the leave-on time, the locks are rinsed and then dried under a drying hood at 40° C.

The colour of the locks was evaluated in the CIE L*a*b* system, using a Minolta CM3600D spectrocolorimeter.

| Composition | pH of applied composition | L* | a* | b* | DE* |
|---|---|---|---|---|---|
| Reference non-lightened pigmented natural hair (TD4) | — | 19.89 | 2.7 | 3.18 | — |
| Lock treated with 87.5 g of composition A and 12.5 g of aqueous hydrogen peroxide solution (50% concentration) | 9.2 | 33.37 | 9.86 | 18.34 | 21.52 |
| Lock treated with 87.5 g of composition B and 12.5 g of aqueous hydrogen peroxide solution (50% concentration) | 9.3 | 44.15 | 9.75 | 25.03 | 33.4 |

The mixture according to the invention derived from composition B of the invention leads to very pronounced levels of lightening which are higher than those with the comparative mixture outside the invention derived from composition A not comprising any potassium pyrophosphate.

Example 2

The following compositions are prepared from the following ingredients in the following proportions, indicated in grams:

|  | compo D invention | compo F invention | compo H invention |
|---|---|---|---|
| Sodium carbonate | 1.8 | 1.8 | 1.8 |
| Potassium pyrophosphate | 5.3 | 5.3 | 5.3 |
| Water | 19.0 | 19.0 | 19.0 |
| Dodecane | 17.6 | 17.6 | 17.6 |
| Benzyl alcohol | 0.9 | 0.9 | 0.9 |
| 1-(2-Butoxy-1-methylethoxy)propan-2-ol | 8.8 | 8.8 | 8.8 |
| Sodium laureth sulfate at 26% in water | 41.9 | 41.9 | 41.9 |
| Pyrophosphoric acid |  |  |  |
| Potassium persulfate | 5 | 5 | 5 |
| pH | 11.3 | 10.5 | 10.1 |

87.5 g of each of the compositions D, F and H were mixed with 12.5 g of aqueous hydrogen peroxide solution (50% concentration) (20-volumes final). The mixtures thus obtained were applied to locks of natural pigmented Caucasian hair with a tone depth of 4 (TD4).

The "mixture/lock" bath ratio is, respectively, 10/1 (g/g).

The leave-on time is 1 hour, on a hotplate set at 40° C. On conclusion of the leave-on time, the locks are rinsed and then dried under a drying hood at 40° C.

The colour of the locks was evaluated in the CIE L*a*b* system, using a Minolta CM3600D spectrocolorimeter.

|  | Composition | pH of applied composition | L* | a* | b* | DE* |
|---|---|---|---|---|---|---|
| Reference non-lightened pigmented natural hair TD4 |  |  | 19.12 | 2.81 | 3.54 | — |
| 87.5 g of composition with 12.5 g of aqueous hydrogen peroxide solution (50% concentration) (20-volumes final) | D | 9.6 | 55.62 | 7.87 | 26.41 | 43.37 |
|  | F | 9.5 | 55.19 | 7.87 | 26.56 | 43.09 |
|  | H | 9.2 | 53.92 | 8.29 | 26.85 | 42.24 |

The compositions according to the invention comprising potassium pyrophosphate and sodium carbonate in the composition give very pronounced levels of lightening.

Example 3

The following compositions were prepared from the following ingredients in the following proportions, indicated in grams:

|  | compo I | compo J | compo K | compo L | compo M | compo N | compo O |
|---|---|---|---|---|---|---|---|
| Sodium carbonate | 4.2 | 4 | 4 | 4 | 4 | 4 | 4 |
| Sodium phytate | 3 | 4 | 4 | 4 | 4 | 3 | 4 |
| Potassium pyrophosphate | 2 | 4 | 1.5 | 4 | 4 | 2 | 4 |
| Water | 23 | 12 | 18.5 | 11 | 21 | 21 | 21 |
| Isododecane | 25 | 25 | 25 | 25 | 25 | 25 | 25 |

-continued

|  | compo I | compo J | compo K | compo L | compo M | compo N | compo O |
|---|---|---|---|---|---|---|---|
| Benzyl alcohol | 3 | 5 | — | — | — | 3 | 1 |
| Phenoxyethanol | — | — | 5 | 5 | — | — | 1 |
| 2-Phenylethanol | — | — | — | — | 3 | — | 1 |
| 1-(2-Butoxy-1-methylethoxy)propan-2-ol | 3 | 0.3 | 2 | 1 | 1.2 | 2.3 | 2.1 |
| Laureth-2 | 1 | — | 1.3 | — | — | 0.5 | — |
| Sodium laureth sulfate at 26% in water | 35.8 | 45.7 | 38.5 | 48 | 38.5 | 38.7 | 36.9 |
| Pyrophosphoric acid | qs 9.9 | qs 9.7 | qs 9.8 | qs 9.7 | qs 9.9 | qs 9.7 | qs 9.7 |
| Potassium persulfate | 5 | 5 | 5 | 5 | 5 | 5 | 5 |
| pH | 9.9 | 9.7 | 9.8 | 9.7 | 9.9 | 9.7 | 9.7 |

87.5 g of each of the compositions I to O were mixed with 12.5 g of aqueous hydrogen peroxide solution (50% concentration) (20-volumes final). The mixtures thus obtained were applied to locks of natural pigmented Caucasian hair with a tone depth of 4 (TD4).

The "mixture/lock" bath ratio is, respectively, 10/1 (g/g).

The leave-on time is 1 hour, on a hotplate set at 40° C. On conclusion of the leave-on time, the locks are rinsed and then dried under a drying hood at 40° C.

The colour of the locks was evaluated in the CIE L*a*b* system, using a Minolta CM3600D spectrocolorimeter.

| Composition | pH of applied composition | L* | a* | b* | DE*/ |
|---|---|---|---|---|---|
| Reference non-lightened pigmented natural hair TD4 |  | 20.16 | 2.76 | 3.48 | — |
| 87.5 g of composition with 12.5 g of aqueous hydrogen peroxide solution (50% concentration) (20-volumes final) | I | 9.1 | 66.92 | 5.93 | 24.66 | 51.43 |
|  | J | 9.0 | 66.8 | 6.02 | 25.51 | 51.69 |
|  | K | 9.0 | 65.81 | 5.98 | 24.3 | 50.28 |
|  | L | 8.9 | 65.55 | 6.37 | 25.9 | 50.76 |
|  | M | 9.1 | 64.78 | 6.03 | 25.15 | 49.72 |
|  | N | 8.9 | 65.82 | 6.13 | 24.1 | 50.22 |
|  | O | 8.9 | 64.98 | 6.04 | 24.51 | 49.62 |

It is seen that the compositions according to the invention lead to very pronounced levels of lightening of the keratin fibres.

Example 4

The following compositions were prepared from the following ingredients in the following proportions, indicated in grams (g of AM per 100 g of composition)

|  | Composition A1 (invention) | Composition B1 (comparative) |
|---|---|---|
| Potassium carbonate | 23.3 | 23.3 |
| Tetrapotassium pyrophosphate | 17.2 | 17.2 |
| Ammonium persulfate | 9.2 | 9.2 |
| Water | qs 100 | qs 100 |

|  | Oxidizing agent |
|---|---|
| 50% hydrogen peroxide solution | 18 |
| Cetearyl alcohol | 8 |
| Ceteareth-33 | 2 |
| Acrylates/beheneth-25 methacrylate copolymer | 2 |
| Tetrasodium pyrophosphate pH agent | 0.04 |
| Tetrasodium etidronate | 0.2 |
| Sodium salicylate | 0.035 |
| Water | qs 100 |

Comparative

Mixture M1=A1+Ox (inv) vs Mixture M2=B1+Ox (comp)

Protocol

At the time of use, the following are mixed together:

1 part by weight of composition A or B 1 part of composition Ox

The pH of mixture M1 of composition A1 with the oxidizing agent Ox is adjusted to 9.2. The pH of the comparative mixture M2 of composition B1 with the oxidizing agent Ox is adjusted to 10.2.

Each mixture is then applied to a natural chestnut-brown lock (tone depth 4).

The "mixture/lock" bath ratio is, respectively, 10/1 (g/g).

The leave-on time is 50 minutes at 33° C., under cover. After this time, the locks are rinsed, and then washed with a standard shampoo and dried.

Colorimetric Measurements

The measurements were taken using a Minolta CM2600d spectrophotometer (illuminant D65, angle 10°, specular component included) in the CIELab system.

In this system, L* represents the lightness. The higher the value of L*, the more the lock is lightened.

Results/Lightening Performance (L)

|  | L* |
|---|---|
| Mixture M1 of pH 9.2 = Composition A1 + Ox (invention) | 62.75 |
| Mixture M2 of pH 10.2 = Composition B1 + Ox (comparative) | 49.52 |

The mixture M1 according to the invention results in a higher value of L*, and thus greater lightening, compared with comparative mixture M2 (according to the prior art).

The invention claimed is:

1. A composition for lightening keratin materials, comprising:
   (a) hydrogen peroxide;
   (b) at least one carbonate or carbonate-generating system in an amount ranging from 0.3% to 15% by weight, relative to the total weight of the composition;
   (c) at least one polyphosphorus derivative, in an amount ranging from 0.55% to 15% by weight, relative to the total weight of the composition; and
   (d) at least one peroxygenated salt;
   wherein the at least one polyphosphorus derivative is different from the at least one peroxygenated salt;
   wherein the pH of the composition is less than or equal to 10;
   wherein the at least one polyphosphorus derivative is chosen from compounds belonging to any one of formulae (I), (II), or (III) below, solvates thereof, or mixtures thereof:

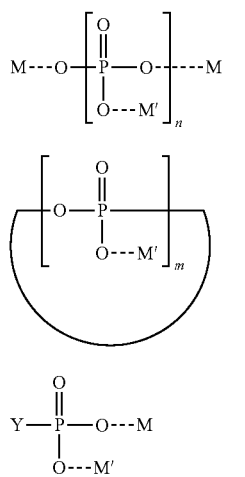

wherein:
   n ranges from 2 to 10;
   m ranges from 2 to 10;
   Y represents an alkyl chain comprising at least one phosphorus atom and optionally one or more non-phosphorus heteroatoms, or a cyclic carbon-based radical optionally comprising one or more heteroatoms, said cyclic carbon-based radical being substituted with one or more groups comprising one or more phosphorus atoms;
   M or M' represents a hydrogen atom, an alkali metal, or an alkaline-earth metal; and
   - - - - represents a single bond when M or M' is H, or an ionic bond; and
   wherein the composition is free of ammonia and ammonium salts.

2. The composition according to claim 1, wherein hydrogen peroxide is present in an amount of from 0.1% to 25% by weight, relative to the total weight of the composition.

3. The composition according to claim 1, wherein (d) the at least one peroxygenated salt is chosen from persulfates, perborates of alkali metals, magnesium peroxide, or mixtures thereof; and wherein the at least one peroxygenated salt is not chosen from ammonium salts.

4. The composition according to claim 1, wherein the at least one peroxygenated salt is present in an amount from 0.01% to 50% by weight, relative to the total weight of the composition.

5. The composition according to claim 1, wherein the at least one carbonate or carbonate-generating system is chosen from carbonates of alkali metals with formula $(Met_2CO_3)$, carbonates of alkaline-earth metals with formula $(Met'CO_3)$, carbonates of phosphonium $(PR''_4)_2CO_3$, or mixtures thereof;
   wherein Met' is an alkaline-earth metal, Met is an alkali metal, and R'', which may be identical or different, is a hydrogen atom or an optionally substituted (C1-C6) alkyl group or (C1-C6) alkoxy group.

6. The composition according to claim 1, wherein the at least one carbonate or carbonate-generating system is chosen from sodium carbonate, potassium carbonate, magnesium carbonate, calcium carbonate, or mixtures thereof.

7. The composition according to claim 1, wherein the at least one carbonate or carbonate-generating system is present in an amount of 0.5% to 10% by weight, relative to the total weight of the composition.

8. The composition according to claim 1, wherein the at least one polyphosphorus derivative is chosen from:
   inorganic polyphosphorus derivatives comprising:
      pyrophosphates in the form of alkali metal salts, which are optionally hydrated;
      hexametaphosphates of alkali metal salts, which are optionally hydrated;
      tripolyphosphates in the form of alkali metal salts, which are optionally hydrated;
      trimetaphosphates in the form of alkali metal salts, which are optionally hydrated; or
      mixtures thereof;
   organic polyphosphorus derivatives comprising:
      organic polyphosphate derivatives;
      organic polyphosphonate derivatives; or
      mixtures thereof; or
   mixtures thereof.

9. The composition according to claim 1, wherein the at least one polyphosphorus derivative is chosen from:
   inorganic polyphosphate derivatives comprising hydrated or non-hydrated alkali metal pyrophosphates, polyphosphates, or mixtures thereof;
   organic polyphosphorus derivatives comprising polyphosphoric acids and/or salts thereof, polyphosphonic acids and/or salts thereof, or mixtures thereof; or
   mixtures thereof.

10. The composition according to claim 1, wherein the at least one polyphosphorus derivative is chosen from sodium pyrophosphate, potassium pyrophosphate, sodium pyrophosphate decahydrate, or mixtures thereof.

11. The composition according to claim 1, wherein the at least one polyphosphorus derivative is present in a total amount ranging from 0.7% to 12% by weight, relative to the total weight of the composition.

12. The composition according to claim 1, wherein the composition further comprises at least one surfactant chosen from anionic or nonionic surfactants.

13. The composition according to claim 1, wherein the composition further comprises at least one fatty substance chosen from hydrocarbons with more than 16 carbon atoms, C6-C16 alkanes, oils or triglycerides of plant origin, liquid synthetic triglycerides, fatty alcohols, esters of a fatty acid and/or of a fatty alcohol other than triglycerides, non-silicone waxes, or mixtures thereof.

14. The composition according to claim 13, wherein the at least one fatty substance is present in a total amount ranging from 5% to 80% by weight, relative to the total weight of the composition.

15. The composition according to claim 1, wherein the composition further comprises at least one liquid organic solvent with a Hansen solubility parameter 5H value of greater than 0 and less than 16 MPa$^{1/2}$ at a temperature of 25° C. and at atmospheric pressure, the at least one liquid organic solvent being chosen from alcohol ethers, aliphatic esters, aliphatic ethers, aromatic ethers, alkanols bearing aryl substituents, lactones, or mixtures thereof, wherein the at least one liquid organic solvent is present in a total amount ranging from 0.1% to 35% by weight, relative to the total weight of the composition.

16. The composition according to claim 1, wherein the pH of the composition ranges from 6 to 9.7.

17. A method for lightening keratin materials, comprising applying to the keratin materials a lightening composition comprising:
 (a) hydrogen peroxide;
 (b) at least one carbonate or carbonate-generating system in an amount of ranging from 0.3% to 15% by weight, relative to the total weight of the lightening composition;
 (c) at least one polyphosphorus derivative, in an amount ranging from 0.55% to 15% by weight, relative to the total weight of the lightening composition; and
 (d) at least one peroxygenated salt;
 wherein the at least one polyphosphorus derivative is different from the at least one peroxygenated salt;
 wherein the pH of the lightening composition is less than or equal to 10;
 wherein the at least one polyphosphorus derivative is chosen from compounds belonging to any one of formulae (I), (II), or (III) below, solvates thereof, or mixtures thereof:

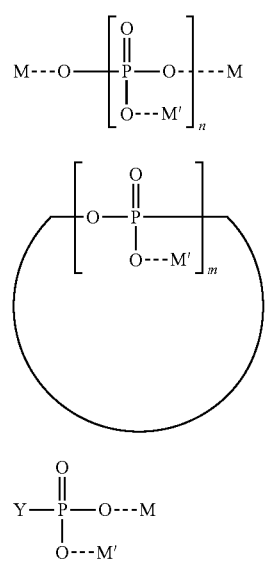

wherein:
 n ranges from 2 to 10;
 m ranges from 2 to 10;
 Y represents an alkyl chain comprising at least one phosphorus atom and optionally one or more non-phosphorus heteroatoms, or a cyclic carbon-based radical optionally comprising one or more heteroatoms, said cyclic carbon-based radical being substituted with one or more groups comprising one or more phosphorus atoms;
 M or M' represents a hydrogen atom, an alkali metal, or an alkaline-earth metal; and
 - - - - represents a single bond when M or M' is H, or an ionic bond; and
wherein the lightening composition is free of ammonia and ammonium salts.

18. The method according to claim 17, further comprising mixing a composition (A) and a composition (B) to obtain the lightening composition, wherein:
 the composition (A) comprises (a) hydrogen peroxide, and (d) at least one peroxygenated salt; and
 the composition (B) comprises (b) at least one carbonate or carbonate-generating system, and (c) at least one polyphosphorus derivative, wherein the at least one polyphosphorus derivative is different from the at least one peroxygenated salt.

19. The method according to claim 17, further comprising mixing a composition (A) and a composition (B) to obtain the lightening composition, wherein:
 the composition (A) comprises (c) at least one polyphosphorus derivative, (a) hydrogen peroxide, and (d) at least one peroxygenated salt, and
 the composition (B) comprises (b) at least one carbonate or carbonate-generating system, and (c) at least one polyphosphorus derivative, wherein the at least one polyphosphorus derivative is different from the at least one peroxygenated salt.

20. The method according to claim 17, further comprising mixing a composition (A), a composition (B), and a composition (C) to obtain the lightening composition, wherein:
 the composition (A) comprises (a) hydrogen peroxide;
 the composition (B) comprises (d) at least one peroxygenated salt; and
 the composition (C) comprises (b) at least one carbonate or carbonate-generating system, and (c) at least one polyphosphorus derivative, wherein the at least one polyphosphorus derivative is different from the at least one peroxygenated salt.

21. A multi-compartment device comprising:
 a first compartment comprising a composition (A) comprising (c) at least one polyphosphorus derivative, (a) hydrogen peroxide, and (d) at least one peroxygenated salt; and
 a second compartment containing a composition (B) comprising (b) at least one or more carbonate or carbonate-generating system, and (c) at least one polyphosphorus derivative;
 wherein the at least one polyphosphorus derivative is different from the at least one peroxygenated salt;
 wherein the at least one polyphosphorus derivative is chosen from compounds belonging to any one of formulae (I), (II), or (III) below, solvates thereof, or mixtures thereof:

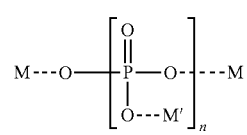

-continued

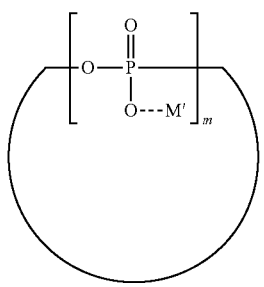
(II)

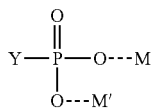
(III)

wherein:
n ranges from 2 to 10;
m ranges from 2 to 10;
Y represents an alkyl chain comprising at least one phosphorus atom and optionally one or more non-phosphorus heteroatoms, or a cyclic carbon-based radical optionally comprising one or more heteroatoms, said cyclic carbon-based radical being substituted with one or more groups comprising one or more phosphorus atoms;
M or M' represents a hydrogen atom, an alkali metal, or an alkaline-earth metal; and
- - - - represents a single bond when M or M' is H, or an ionic bond;
wherein a mix of the compositions of the compartments results in a lightening composition comprising (c) the at least one polyphosphorus derivative in an amount ranging from 0.55% to 15% by weight, relative to the total weight of the lightening composition, and (b) the at least one carbonate or carbonate-generating system in an amount ranging from 0.3% to 15% by weight, relative to the total weight of the lightening composition;
wherein the pH of the lightening composition is less than or equal to 10; and
wherein the lightening composition is free of ammonia and ammonium salts.

22. A multi-compartment device comprising:
a first compartment containing composition (A) comprising (a) hydrogen peroxide;
a second compartment containing composition (B) comprising (d) at least one peroxygenated salt; and
a third compartment containing composition (C) comprising (b) at least one carbonate or carbonate-generating system, and (c) at least one polyphosphorus derivative;
wherein the at least one polyphosphorus derivative is different from the at least one peroxygenated salt;
wherein the at least one polyphosphorus derivative is chosen from compounds belonging to any one of formulae (I), (II), or (III) below, solvates thereof, or mixtures thereof:

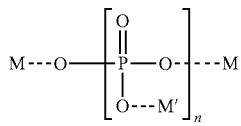
(I)

(II)

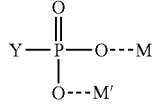
(III)

wherein:
n ranges from 2 to 10;
m ranges from 2 to 10;
Y represents an alkyl chain comprising at least one phosphorus atom and optionally one or more non-phosphorus heteroatoms, or a cyclic carbon-based radical optionally comprising one or more heteroatoms, said cyclic carbon-based radical being substituted with one or more groups comprising one or more phosphorus atoms;
M or M' represents a hydrogen atom, an alkali metal, or an alkaline-earth metal; and
- - - represents a single bond when M or M' is H, or an ionic bond;
wherein a mix of the compositions of the compartments results in a lightening composition comprising (c) the at least one polyphosphorus derivative in an amount ranging from 0.55% to 15% by weight, relative to the total weight of the lightening composition, and (b) the at least one carbonate or carbonate-generating system, in an amount ranging from 0.3% to 15% by weight, relative to the total weight of the lightening composition;
wherein the pH of the lightening composition is less than or equal to 10; and
wherein the lightening composition is free of ammonia and ammonium salts.

* * * * *

UNITED STATES PATENT AND TRADEMARK OFFICE
CERTIFICATE OF CORRECTION

| | | |
|---|---|---|
| PATENT NO. | : 12,064,500 B2 | Page 1 of 1 |
| APPLICATION NO. | : 16/468354 | |
| DATED | : August 20, 2024 | |
| INVENTOR(S) | : Alain Lagange et al. | |

It is certified that error appears in the above-identified patent and that said Letters Patent is hereby corrected as shown below:

In the Claims

Claim 15, Column 41, Line 7, please change "5H" to -- $\delta$H --.

Signed and Sealed this
Seventeenth Day of December, 2024

Derrick Brent
*Acting Director of the United States Patent and Trademark Office*